United States Patent
Saidian et al.

(10) Patent No.: US 10,551,520 B2
(45) Date of Patent: Feb. 4, 2020

(54) SURFACE RELAXIVITY CALCULATION USING NUCLEAR MAGNETIC RESONANCE (NMR) MEASUREMENT, THREE DIMENSIONAL (3D) ROCK MODEL AND NMR RESPONSE SIMULATION

(71) Applicant: Colorado School of Mines, Golden, CO (US)

(72) Inventors: Milad Saidian, Houston, TX (US); Manika Prasad, Golden, CO (US)

(73) Assignee: Colorado School of Mines, Golden, CO (US)

( * ) Notice: Subject to any disclaimer, the term of this patent is extended or adjusted under 35 U.S.C. 154(b) by 993 days.

(21) Appl. No.: 14/941,310

(22) Filed: Nov. 13, 2015

(65) Prior Publication Data

US 2016/0139291 A1    May 19, 2016

Related U.S. Application Data

(60) Provisional application No. 62/079,481, filed on Nov. 13, 2014.

(51) Int. Cl.
*G01V 3/32* (2006.01)
*G01N 24/08* (2006.01)

(52) U.S. Cl.
CPC ............. *G01V 3/32* (2013.01); *G01N 24/081* (2013.01)

(58) Field of Classification Search
CPC ....... G01V 3/32; G01N 24/081; G01R 33/448
USPC ........................................................ 324/303
See application file for complete search history.

(56) References Cited

U.S. PATENT DOCUMENTS

| | | | |
|---|---|---|---|
| 3,419,795 A | 12/1968 | Genthe et al. | |
| 4,785,245 A | 11/1988 | Lew et al. | |
| 2003/0009297 A1 | 1/2003 | Mirotchnik et al. | |
| 2008/0221800 A1* | 9/2008 | Gladkikh | G01V 3/32 702/11 |
| 2009/0256562 A1 | 10/2009 | Gao et al. | |
| 2012/0209541 A1 | 8/2012 | Ong et al. | |
| 2014/0002081 A1* | 1/2014 | Mitchell | G01N 24/081 324/309 |
| 2014/0026786 A1 | 1/2014 | Jaffel | |

OTHER PUBLICATIONS

Aichele et al., "Water in oil emulsion droplet size characterization using a pulsed field gradient with diffusion editing (PFG-DE) NMR technique," Journal of Colloid and Interface Science, 2007, vol. 315, No. 2, pp. 607-619.

Alcantar-Lopez et al., "Improving Our Understanding of Porosity in Source Rock Reservoirs through Advanced Imaging Techniques," Unconventional Resources Technology Conference, URTeC 1619700, Aug. 2013, abstract only.

Aliyev, "Rock Typing in Tight Gas Sands: A Case Study in Lance and Mesaverde Formations from Jonah Field," M.S. Thesis, Colorado School of Mines, 2015, retrieved from https://dspace.library.colostate.edu/bitstream/handle/11124/20145/Aliyev_mines_0052N_10780.pdf?sequence=1, 83 pages.

(Continued)

*Primary Examiner* — Reena Aurora
(74) *Attorney, Agent, or Firm* — Sheridan Ross PC

(57) ABSTRACT

The present invention is directed to a method to use nuclear magnetic resonance ("NMR") to determine the surface relaxivity in a reservoir. The surface relaxivity can be used to calculate the pore size distribution in a reservoir.

19 Claims, 16 Drawing Sheets

(56) References Cited

OTHER PUBLICATIONS

Allen et al., "How to Use Borehole Nuclear Magnetic Resonance," Oilfield Review, 1997, pp. 34-57.
Ambrose et al., "New Pore-scale Considerations for Shale Gas in Place Calculations," Society of Petroleum Engineers Unconventional Gas Conference, SPE-131772, 2010, 17 pages.
Andra et al., "Digital rock physics benchmarks—Part I: Imaging and segmentation," Computers and Geosciences, vol. 5, 2013, pp. 25-32.
Balinov et al., "The NMR Self-Diffusion Method Applied to Restricted Diffusion. Simulation of Echo Attenuation from Molecules in Spheres and between Planes," Journal of Magnetic Resonance Series A, vol. 104, No. 1, Aug. 1993, pp. 17-25.
Barrett et al., "The Determination of Pore Volume and Area Distributions in Porous Substances: I. Computations From Nitrogen Isotherms," Journal of the American Chemicy Society, vol. 73, No. 1, Jan. 1951, pp. 373-380.
Brown et al., "Southern Piceance Basin Model—Cozzette, Corcoran and Rollins Sandstones," American Association of Petroleum Geologists Studies in Geology, vol. 24, 1986, pp. 207-219, abstract only.
Buess et al., "Acoustic ringing effects in pulsed nuclear magnetic resonance probes," Review of Scientific Instruments, vol. 49, No. 8, 1978, pp. 1151-1155, abstract only.
Butler et al., "Estimating Solutions of First Kind Integral Equations with Nonnegative Constraints and Optimal Smoothing," SIAM Journal of Numerical Analysis, vol. 18, No. 3, 1981, pp. 381-397, abstract only.
Carr et al., "Effects of Diffusion on Free Precession in Nuclear Magnetic Resonance Experiments," Physical Review, vol. 94, No. 3, May 1954, pp. 630-638, abstract only.
Chan et al., "Characterization and correction of eddy-current artifacts in unipolar and bipolar diffusion sequences using magnetic field monitoring," Journal of Magnetic Resonance, vol. 224, Jul. 2014, pp. 74-84.
Chi et al., "Quantifying the Impact of Natural Fractures and Pore Structure on NMR Measurements in Multiple-Porosity Systems," International Petroleum Technology Conference, Jan. 2014, 12 pages, abstract only.
Coates et al., "NMR Logging Principles and Applications," Haliburton Energy Services Publication, 1999, 251 pages, multiple parts.
Delgado-Linares et al., "Model Water-in-Oil Emulsions for Gas Hydrate Studies in Oil Continuous Systems," Energy Fuels, 2013, vol. 27, No. 8, pp. 4564-4573, 10 pages.
Dunn et al., "Nuclear Magnetic Resonance Petrophysical and Logging Applications," 1st edition, Pergamon, 2002, vol. 32, abstract only, 3 pages.
Dunn et al., "On the Calculation of NMR Relaxation Time Distributions," Society of Petroleum Engineers Annual Technical Conference and Exhibition, SPE-28367, 1994, 10 pages, abstract only.
Freedman et al., "Wettability, Saturation, and Viscosity Using the Magnetic Resonance Fluid Characterization Method and New Diffusion-Editing Pulse Sequences," Society of Petroleum Engineers Annual Technical Conference and Exhibition, SPE-77397-MS, Sep. 2002, 13 pages, abstract only.
Fridjonsson et al., "Determination of mean droplet sizes of water-in-oil emulsions using an Earth's field NMR instruction," Journal of Magnetic Resonance, 2012, vol. 221, pp. 97-102.
Harkins et al., "Surfaces of Solids. XII, An Absolute Method for the Determination of the Area of a Finely Divided Crystalline Solid," Journal of the American Chemical Society, vol. 66, No. 8, 1944, pp. 1362-1366, abstract only.
Howard, "Porosimetry Measurement of Shale Fabric and its Relationship to Illite/Smectite Diagenesis," Clays and Clay Minerals, vol. 39, No. 4, 1991, pp. 355-361.
Hurlimann et al., "Diffusion-Editing: New NMR Measurement of Saturation and Pore Geometry," Society of Petrophysicists and Well-Log Analysts, 2002, SPWLA 43rd Annual Logging Symposium, Oiso, Japan, abstract only, 2 pages.
Hurlimann et al., "Quantitative Measurement of Two-Dimensional Distribution Functions of Diffusion and Relaxation in Grossly Inhomogeneous Fields," Journal of Magnetic Resonance, vol. 157, No. 1, Jul. 2002, pp. 31-42, abstract only.
Hurlimann, "Effective Gradients in Porous Media Due to Susceptibility Differences," Journal of Magnetic Resonance, vol. 131, No. 2, Apr. 1998, pp. 232-240, abstract only.
Jiang et al., "Integrated Petrophysical Interpretation of Eagle Ford Shale with 1-D and 2-D Nuclear Magnetic Resonance (NMR)," Society of Petrophysicists and Well Log Analysts Annual Logging Symposium, No. 54, Jun. 2013, 22 pages, abstract only.
Johns, "NMR studies of emulsions," Current Opinion in Colloid & Interface Science, 2009, vol. 14(3), pp. 178-183, abstract only, 2 pages.
Kenyon, "Nuclear magnetic resonance as a petrophysical measurement," Nuclear Geophysics, vol. 6, No. 2, 1992, pp. 153-171, abstract only.
Kenyon, "Petrophysical Principles of Applications of NMR Logging," The Log Analyst vol. 38, No. 2, Mar. 1997, 23 pages, abstract only.
Kleinberg, "NMR Well Logging at Schlumberger," Concepts in Magnetic Resonance, vol. 13, No. 6, 2001, pp. 396-403.
Kulia et al., "Compositional Controls on Mudrock Pore-Size Distribution: An Example from Niobrara Formation," SPE Annual Technical Conference and Exhibition, Oct. 2012, abstract only.
Kulia et al., "Measurement and interpretation of porosity and pore-size distribution in mudrocks: The hole story of shales," Ph.D. Thesis, Colorado School of Mines, 2013, 269 pages.
Kulia et al,, "Specific surface area and pore-size distribution in clays and shales," Geophysical Prospecting, vol. 61, 2013, pp. 341-362.
Latorraca et al., "Heavy Oil Viscosity Determination Using NMR Logs," SPWLA 40th Annual Logging Symposium, May 1999, abstract only.
Latour et al., "Pore-Size Distributions and Tortuosity in Heterogeneous Porous Media," Journal of Magnetic Resonance A, vol. 112, No. 1, Jan. 1995, pp. 83-91, abstract only.
Lewis et al., "NMR T2 Distributions in the Eagle Ford Shale: Reflections on Pore Size," SPE Unconventional Resources Technology Conference Paper No. 164554, 2013,15 pages, abstract only.
Machado et al., "Carbonate Petrophysics in Wells Drilled with Oil-Base Mud," SPWLA 52nd Annual Logging Symposium, May 2011, 10 pages.
Marschall et al., "Method for Correlating NMR Relaxometry and Mercury Injection Data," SCA Conference Paper No. 9511, 1995, 12 pages.
Meiboom et al., "Modified SpinEcho Method for Measuring Nuclear Relaxation Times," AIP Review of Scientific Instruments, vol. 29, No. 8, Aug. 1958, pp. 688-691.
Mitra et al., "Effects of microgeometry and surface relaxation on NMR pulsed-field-gradient experiments: Simple pore geometries," Physics Review B., vol. 45, No. 1, Jan. 1992, pp. 143-156, abstract only.
Opedal et al., "Methods for Droplet Size Distribution Determination of Water-in-oil Emulsions Using Low-Field NMR," Journal for the Basic Principles of Diffusion Theory, Experiment and Application, 2009, vol. 9, pp. 1-29.
Packer et al., "Pulsed NMR Studies of Restricted Diffusion: I. Droplet size distribution," Journal of Colloid and Interface Science, 1971, vol. 40, No. 2, pp. 206-218, abstract only, 2 pages.
Pape et al., "Pore geometry of sandstone derived from pulsed field gradient NMR," Journal of Applied Geophysics, vol. 58, No. 3, Mar. 2006, pp. 232-252, abstract only.
Passey et al., "From Oil-Prone Source Rock to Gas-Producing Shale Reservoir—Geologic and Petrophysical Characterization of Unconventional Shale-Gas Reservoirs," Society of Petroleum Engineers, SPE Paper No. 131350, Jun. 2010, 29 pages.
Peixinho et al., "Rheology of Hydrate Forming Emulsions," American Chemical Society, 2010, vol. 26, No. 14, pp. 11699-11704.
Pena et al., "Enhanced characterization of oilfield emulsions via NMR diffusion and transverse relaxation experiments," Advances in Colloid and Interface Science, 2003, vol. 105, pp. 103-150.

(56) References Cited

OTHER PUBLICATIONS

Price, "Pulsed-Field Gradient Nuclear Magnetic Resonance as a Tool for Studying Translational Diffusion: Part 1. Basic Theory," Concepts in Magnetic Resonance, vol. 9, No. 5, 1997, pp. 299-336.
Rivera et al., "Effect of Mineralogy on NMR, Sonic, and Resistivity: A Case Study of the Monterey Formation," SPE Unconventional Resources Technology Conference Paper No. 1922872, 2014, 20 pages.
Song, "Recent progress of nuclear magnetic resonance applications in sandstones and carbonates rocks," Vadose Zone Journal, 2010, vol. 9, pp. 828-834.
Sorland et al., "Rapid characterization of emulsions by pulsed field gradient nuclear magnetic resonance," Journal for the Basic Principles of Diffusion Theory, Experiment and Application, 2013, vol. 19, pp. 1-16.
Stejskal et al., "Spin Diffusion Measurements: Spin Echoes in the Presence of a Time-Dependent Field Gradient," Journal of Chemical Physics, vol. 42, No. 1, Jan. 1965, pp. 288-292.
Straley et al., "Core Analysis by Low Field NMR," Log Analyst, vol. 38, No. 2, 1994, p. 43-56.
Sun et al., "Two-dimensional nuclear magnetic resonance petrophysics," Magnetic Resonance Imaging, vol. 23, No. 2, Feb, 2005, pp. 259-262, abstract only.
Talabai, "Pore-Scale Simulation of NMR Response in Porous Media," Ph.D. Thesis, Imperial College, Sep. 2008, 163 pages.
Tanner, "Use of Stimulated Echo in NMR Diffusion Studies," Journal of Chemical Physics, vol. 52, No. 5, 1970, pp. 2523-2526, abstract only.
Timur, "Pulsed Nuclear Magnetic Resonance Studies of Porosity, Movable Fluid, and Permeability of Sandstones," Journal of Petroleum Technology, vol. 21, No. 6, Jun. 1969, 12 pages, abstract only.
Toumelin et al., "Limits of 2D NMR Interpretation Techniques to Quantify Pore Size, Wettability, and Fluid Type: A Numerical Sensitivity Study," SPE Journal, vol. 11, No. 3, Sep. 2006, pp. 354-363.
Turner et al., "Methane hydrate formation and an inward growing shell model in water-in-oil dispersions," Chemical Engineering Science, 2009, vol. 64, No. 18, pp. 3996-4004.
Venkataramanan et al., "Solving Fredholm integrals of the first kind with tensor product structure in 2 and 2.5 dimensions," IEEE Transactions on Signal Processing, 2002, vol. 50, No. 5, pp. 1017-1026, abstract only, 4 pages.
Whittal et al., "Quantitative interpretation of NMR relaxation data," Journal of Magnetic Resonance, vol. 84, No. 1, Aug. 1989, pp. 134-152, abstract only.
Official Action for U.S. Appl. No. 15/143,000, dated Sep. 20, 2018, 9 pages.
Notice of Allowance for U.S. Appl. No. 15/143,000, dated Oct. 16, 2019 6 pages.

\* cited by examiner

SURFACE RELAXIVITY CALCULATION USING NUCLEAR MAGNETIC RESONANCE (NMR) MEASUREMENT, THREE DIMENSIONAL (3D) ROCK MODEL AND NMR RESPONSE SIMULATION

CROSS REFERENCE TO RELATED APPLICATIONS

This application claims priority under 35 U.S.C. § 119(e) to U.S. Provisional Patent Application Ser. No. 62/079,481 filed on Nov. 13, 2014, which is incorporated herein in its entirety by reference.

FIELD OF THE INVENTION

The invention relates to a method of using surface relaxivity to calculate the pore size distribution in petroleum applications.

BACKGROUND

Pore size distribution is a crucial parameter which is required to evaluate reservoir producibility and rock quality for petrochemical applications. The only direct downhole representation of the pore size distribution is nuclear magnetic resonance ("NMR") logging $T_2$ distribution data. In petroleum engineering applications, the pore size distribution is in the size domain whereas the $T_2$ distribution is in the time domain. A reliable estimate of surface relaxivity is required to convert time domain $T_2$ data to size domain pore size distribution. The available techniques to estimate the surface relaxivity are in the form of correlations and do not apply in rocks with very fine grains such as shales.

Although $T_2$ distribution is a representation of the pore size distribution, it is plotted in time domain rather than size domain. Surface relaxivity is the key parameter to convert NMR $T_2$ distribution to size distribution. Direct measurement and calculation of surface relaxation is a challenging task for both conventional and unconventional rocks. The common methodology is to correlate pore/throat size distribution measurements such as mercury intrusion or nitrogen adsorption with NMR. Using this method, an estimate of surface relaxivity is calculated for downhole logging applications. The main disadvantage of this method is inability to assess the whole pore network due to pore accessibility limitations.

SUMMARY

The present invention overcomes this disadvantage with a work flow for calculating surface relaxivity using The Focused Ion Beam Scanning Electron Microscope ("FIB-SEM"), 3D digital rock models and nuclear magnetic resonance ("NMR") simulation. In the present method, a combination of techniques and technologies can be used to calculate the surface relaxivity of the rock and convert time domain NMR data to size domain pore size distribution.

The present invention provides a method to precisely calculate the surface relaxivity by combining NMR measurement (in some embodiments, NMR laboratory measurements), 3D rock models and NMR simulation. The method can be used for downhole NMR log analysis and interpretation, which is especially useful for commercial and research petroleum applications. Embodiments of the invention include a complementary approach for surface relaxivity calculation using FIBSEM 3D rock models and NMR simulation.

"Rock Typing in Tight Gas Sands: A Case Study in Lance and Mesaverde Formations from Jonah Field" by Elshan Aliyev (2015) is incorporated by reference herein in its entirety.

In one embodiment, a method to calculate a pore size distribution in a hydrocarbon reservoir is provided comprising: determining a simulated T2 distribution; determining an experimental T2 distribution; determining the surface relaxivity with the simulate T2 distribution and the experimental T2 distribution; determining a pore size distribution with a surface relaxivity; and comparing the surface relaxivity with an experimental pore size distribution to determine the pore size distribution in the hydrocarbon reservoir. In further embodiments, the method further comprises comparing the surface relaxivity with a laboratory NMR response to determine an adjusted surface relaxivity and converting a NMR size distribution to the pore size distribution with the adjusted surface relaxivity. In various embodiments, the method further comprises comparing an independent pore size distribution measurement with the pore size distribution, wherein the independent pore size distribution measurement is obtained by at least one of mercury intrusion or nitrogen adsorption.

DETAILED DESCRIPTION

The present invention relates to a method that combines NMR measurements, 3D rock models and NMR simulation. The method of the present invention can be used to precisely calculate the surface relaxivity by combining NMR laboratory measurement, 3D rock models and NMR simulation.

Figure 1:
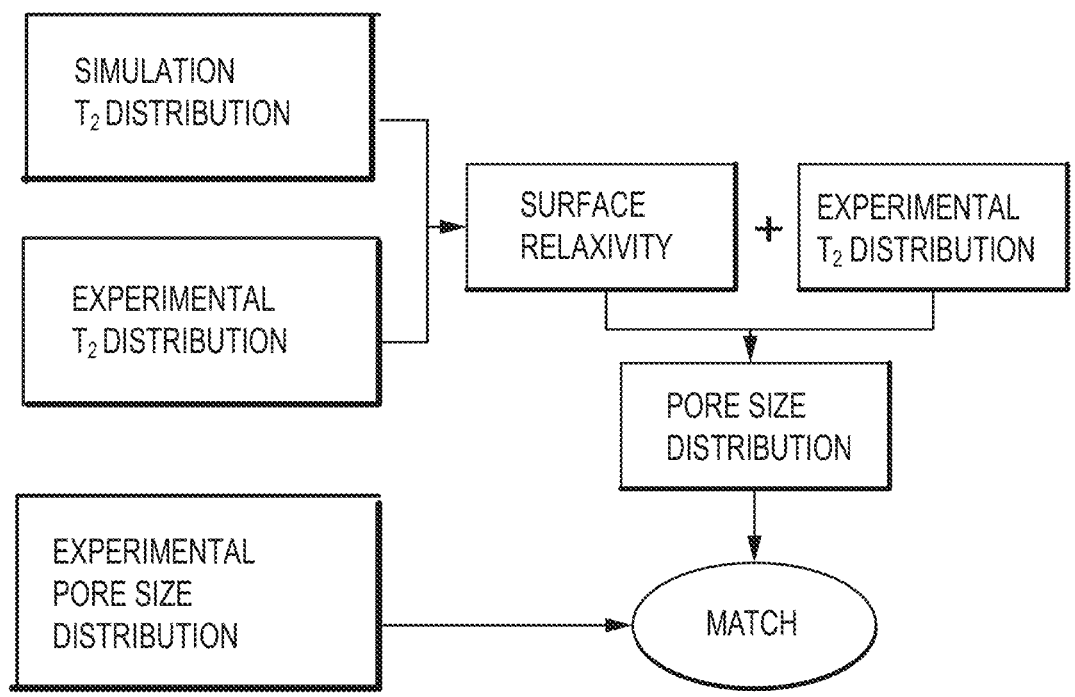
FIG. 1 illustrates a summary of the proposed workflow to calculate the pore size distribution from NMR $T_2$ distribution using NMR simulation in 3D digital rocks.

The final goal for NMR simulation is to calculate the surface relaxivity in challenging samples such rocks, for example mudrocks. Laboratory NMR measurement, 3D rock models and pore size distribution using any measurement technique are determined. FIG. 1 illustrates the flow diagram of the overall method. The $T_2$ distribution for the sample is measured in laboratory or with actual measurements with appropriate acquisition parameters and inversion. The simulated NMR response using different surface relaxivities is compared with the laboratory NMR response to find the surface relaxivity of the sample. The calculations are run using different surface relaxivities, as described herein. The calculated surface relaxivity is used to convert the NMR size distribution to pore size distribution. An independent pore size distribution measurement, such as mercury intrusion or nitrogen adsorption, is required to see whether the proposed methodology results in similar pore size distribution to other measurement techniques or not. Summary of the proposed work flow is illustrated in FIG. 10.

An aspect of the present invention is a method to calculate a pore size distribution in a hydrocarbon reservoir. The method includes determining a simulated $T_2$ distribution and an experimental $T_2$ distribution. The surface relaxivity is determined using the simulated $T_2$ distribution and the experimental $T_2$ distribution. Because the pore size distribution is determined from the digital image, the $T_2$ relaxations are converted to pore size distributions by varying the surface relaxivity to match the digitally-determined surface relaxivity. The experimental pore size distribution is determined using the surface relaxivity. The experimental pore size distribution can be determined using various means. In one embodiment, the experimental pore size distribution is determined using the digital images. In another embodiment, the experimental pore size distribution is measured using gas adsorption or mercury intrusion porosimetry ("MIP").

In some embodiments, the experimental pore size distribution can be compared to the measured pore size distribution of the reservoir. The comparisons have limitations since the experiments might not catch all the pores, for example, MIP does not measure small pores and gas adsorption does not measure large pores.

Experimental NMR $T_2$ Measurement

The NMR technique measures the hydrogen nuclei concentration (detectable by the NMR instrument) in the rock which directly translates to pore volume and in turn to porosity with proper calibrations. Reliable NMR porosity and pore size distribution ("PSD") measurements depend on surface relaxivity of the pores and tool resolution. The main advantage of the NMR tool is that the response is mineral independent. Low frequency NMR is sensitive to the hydrogen molecules in the fluid so the type of the fluid and its composition affects the NMR response. The main disadvantage of the prior art technique is inability to capture the signal from very fast relaxing hydrogens in the rock such as clay hydroxyl groups, kerogen and possibly bitumen, due to instrument limitations. The signal from these hydrogen nuclei relaxes before the NMR acquisition starts.

Determining the experimental $T_2$ distribution is a standard low-field NMR experiment. In some embodiments, a Magritek 2 MHz system is used for this step. In other embodiments, a system by Oxford Instruments is used for this step. For example, samples are put in a magnetic field that orients hydrogen nuclei in the magnetic field. The samples are then subjected to a sequence of pulses, which can be a CMPG pulse sequence in some embodiments. The relaxation time of the hydrogen molecules from their oriented state to their normal state is called $T_2$ relaxation.

NMR measures the hydrogen nuclei concentration and $T_2$ distribution. Depending on tool resolution and grain surface properties, the minimum measurable pore size varies. The minimum measurable pore size is determined from the echo spacing. For example a NMR tool with echo spacing of about 60 μsec can detect hydrogen nuclei in a spherical pore with surface relaxivity of 10 about μm/sec and radius larger than about 1.8 nm. Due to the dominance of surface relaxation, smaller pores have faster relaxation compared to bigger pores. At constant surface relaxivity in a typical $T_2$ distribution, faster relaxation times correlate with smaller pores.

Nuclear magnetic resonance (NMR) is widely used to measure porosity and pore size distributions of high porosity rocks in the laboratory and at downhole conditions. Tight, low-porosity, multi-mineralic, organic-rich rocks (known as shales or mudrocks) are characterized by fast relaxing NMR signals with low amplitude. Considering these requirements, we discuss quality assurance of NMR data acquisition parameters and critical parameters for NMR data processing as applicable to mudrocks (shales). To address the significance of NMR data acquisition parameters, we compare experimental NMR data for a sandstone and a mudrock. We also use simulations to assess the differences between mathematical inversions and restricted diffusion in simulated sandstone and mudrock responses.

NMR data quality is affected by echo spacing (TE), acquisition delays, number of echoes, and background signals. To capture the fast relaxation in the micropores of mudrocks, a balance must be reached between NMR data acquisition with the smallest TE that is still large enough minimize contributions from acoustic ringing and background signal. The background signal is created by sample holders, plastic warps and air moisture. Uncorrected background signals can be interpreted as micropores.

After acquisition, the NMR data must be processed to get relaxation times. All inversions need to be optimized for three major control factors: smoothing, signal to noise ratio (SNR) and relaxation rate. Our simulations show that (a) the mathematically calculated smoothing parameter oversmoothes the T2 distribution in mud rocks and (b) even at very high signal to noise ratio (>100), the fast relaxing hydrogen nuclei prevent the inversions to capture multimodal pore size distributions.

Models of attenuation due to diffusion with a Gaussian phase distribution (GPD) and short gradient pulse (SGP) reveal that in nano-meter sized pores, large gradient must be applied for the spins to diffuse. Low frequency (2 MHz) logging and laboratory devices with maximum gradient amplitude of 0.5 T or less are not able to measure diffusion in pores smaller than 5 μm because the fast relaxing spins relax before the acquisition starts. Our work can help design optimal conditions for NMR data acquisition and assess its limitations to measure the complex pore structure of mudrocks.

Wireline NMR logs are used to measure porosity and assess pore size distributions in high porosity sandstone and carbonate formations (Kleinberg, 2001). Technological advances in hydraulic fracturing and horizontal drilling have made economic production of oil and gas from tight mudrocks (unconventionals or shales) viable. The term "unconventional reservoir" encompasses a wide range of lithologies or hydrocarbon bearing rocks. In this paper, we refer to tight oil, or gas-producing reservoirs which may or may not be organic rich and are often called "shales". Shales can be either siliciclastic or carbonate mudrocks and are not necessarily clay-rich. In this study we use the terms shale and mudrock interchangeably to denote low-porosity, low-permeability materials with complex mineralogy and possibly organic-rich. With increasing application in mudrocks, the procedures and assumptions required interpreting NMR data for porosity and pore size distributions need to be examined critically for specific requirements to characterize mudrocks.

Porosity and pore size distribution data are crucial for reservoir quality and volume evaluation (Ambrose et al., 2010). Pore size distribution can be used to evaluate permeability (Nelson, 2009), and to calculate elastic properties (Kuila and Prasad, 2011). There are numerous ways to assess the pore size distribution of mudrocks, for example, scanning electron microscopy (Alcantar-Lopez and Chipera, 2013; Zargari et al., 2013; Saidian et al., 2015a), CT-scanning (Milliken et al., 2013), mercury intrusion (Howard, 1991; Rivera et al., 2014; Saidian et al., 2015a), Nitrogen adsorption (Kuila et al., 2012; Saidian et al., 2015a), and NMR (Sondergeld et al., 2010; Jiang et al., 2013; Rylander et al., 2013; Rivera et al., 2014, Saidian et al., 2015b). Amongst these methods, only the NMR technique allows us to assess pore size distributions in the laboratory and at downhole conditions. NMR experiments are a two-part process; data acquisition requiring fit-for-purpose pulse sequences and data processing with carefully designed mathematical inversions. Before using the methods developed for high-porosity rocks, we need to assess whether the specific settings and assumptions can be applied and how they need to be modified for mudrock applications.

The low-field (2 MHz) NMR signal is produced by the hydrogen nuclei present in the pore fluid of porous formations. The concentration of hydrogen is correlated to the porosity of the rock (Kenyon, 1997). Since NMR signals from the minerals cannot be detected by the low-field NMR tool, porosity can be calculated directly without making assumptions about the mineral constituents (Dunn et al., 2002). The relaxation rate of the hydrogen nuclei subjected to an oscillating magnetic field provides information about both, the pore structure and the saturating pore fluid (Kenyon, 1992). Pore size distribution by analyzing $T_1$ and $T_2$ time distributions (Kenyon, 1997), bound and free fluid volume calculations by defining time cut offs (Timur, 1969, Straley et el., 1997 and Coates et al., 1999), permeability estimation using the time distribution spectra (Timur, 1969, Howard et al., 1993 and Kenyon, 1997), fluid typing, saturation (Hürlimann et al., 2002) and viscosity (Latorraca et al., 1999 and Hirasaki et al., 2003) estimation based on fluid relaxation times are some of the common applications of NMR downhole data for conventional rocks such as sandstones and carbonates. However, successful rock and fluid characterizations from NMR data rely on high quality data and data processing. In unconventional rocks, these tasks are more challenging due to small pores, high surface to volume ratio (Saidian et al., 2015a), presence of kerogen and bitumen, occurrence of both mineral-hosted and organic-hosted pores, and abundance of iron bearing minerals such as pyrite (Passey et al., 2010).

NMR signals are acquired using pulse sequences consisting of radio frequency pulses and delay times. Choosing the appropriate acquisition parameters demands an understanding of the pulse sequence, pore structure and fluid properties. For example, the relaxation time of a bulk fluid is inversely proportional to its viscosity (Hirasaki et al., 2003) and is reduced on contact with the grain surfaces in porous media (Dunn et al., 2002). This decrease in relaxation rate depends on the pore characteristics such as pore size, connectivity, mineralogy and surface area to volume ratio (Saidian et al., 2015b). NMR data acquisition in fast relaxing systems such as low porosity rocks, require instruments with high sensitivity and modified pulse sequence timings. In the first part of our paper, we discuss the specific differences in acquisition design for high-porosity sandstones and low-porosity mudstones.

Even the highest quality NMR data must be processed prior to any interpretation of, for example, porosity and pore size distributions. Typically, an inverse Laplace transform (Butler et al., 1981 and Dunn et al., 1994) is applied to account for the relaxation rates superimposed in the NMR raw decay data in the form of a multi-exponential decay. A single exponential decay is usually suitable for inversion of most of low viscosity bulk fluids (Dunn et al., 1994), while fluid saturated porous media often require a multi-exponential decay. In fast relaxing and low porosity rocks, the inversion is usually compromised due to low signal to noise ratio and fast decay of NMR signal. A second part of our paper deals with inversion parameters for high-porosity sandstones and low-porosity mudstones.

Given the increasing application of NMR studies in low porosity, tight rocks, a discussion of the challenges associated with NMR data acquisition and processing in low porosity, tight rocks, though essential, is lacking Note that we do not intent to present new techniques or pulse sequences for NMR data acquisition in unconventional rocks or introduce new inversion algorithm. Our goal was to identify the data acquisition, analysis and interpretation challenges for low-porosity, tight formations and emphasize factors that increase accuracy and reliability of NMR measurements in these samples. We focused on two most common NMR downhole measurements, namely, the transverse relaxation time ($T_2$) mainly used for pore size distribution measurement and 2d diffusion-$T_2$ (D-$T_2$) maps used for fluid identification based on diffusion coefficient differences between reservoir fluids (Hürlimann et al., 2002). We compare NMR response in a sandstone sample and a mudrock sample and show how different acquisition parameters affect the NMR response of each rock. We also use 1D simulation software to investigate the road blocks during mathematical inversion for mudrock samples. We assess the challenges in diffusion measurement by simulating the diffusion response in mudrocks with two analytical models of simplified pore geometries such as spheres.

Before discussing the challenges associated with NMR measurements in shales, we briefly introduce the pulse sequences, inversion algorithms and theoretical models to be used in this study. We focus here on the pulse sequences of two most common downhole NMR measurements; $T_2$ relaxations and D-$T_2$ maps, the theoretical basis and assumptions of the inversion algorithms and the theoretical diffusion models underlying the simulation software used here.

Figure 6:
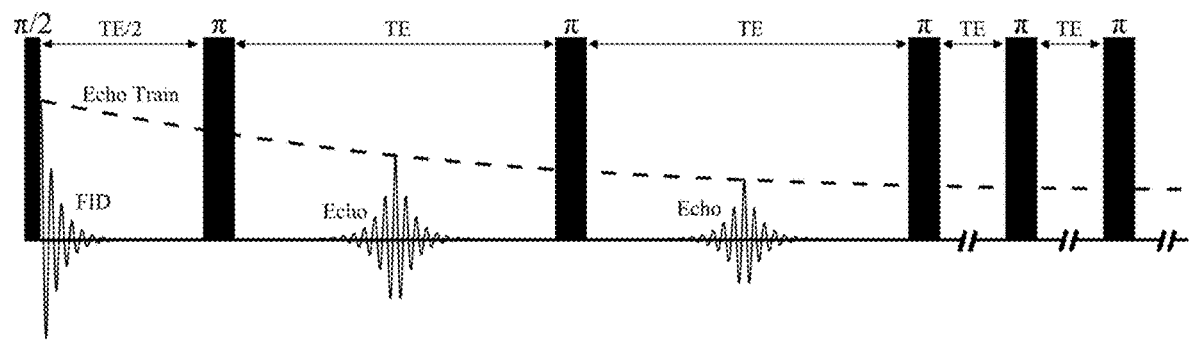
FIG. 6 illustrates a schematic of the CPMG pulse sequence.

$T_2$ measurements are based on the Carr-Purcell-Meiboom-Gill (CPMG) pulse sequence (FIG. 6) (Carr and Purcell, 1954; Meiboom and Gill, 1958). Briefly, this pulse sequence consists of one 90° ($\pi/2$) pulse followed by a number of 180° ($\pi$) pulses (number of echoes) separated by echo spacing (echo time or TE). The loss in magnetization after the 90° pulse is termed as the free induction decay (FID). The coherence of the spins after each 180° or $\pi$ pulse are recorded as pulse spin echoes or simply, echoes (FIG. 6). The CPMG pulse sequence produces a number of spin echoes (number of echoes) that constitute the spin echo train data. This echo train is the raw data for $T_2$ distributions. Pulse length and amplitude, TE and number of echoes are the main parameters that need to be designed according to rock and fluid properties.

FIG. 6: Schematic of the CPMG pulse sequence. This pulse sequence is the most common sequence to measure the $T_2$ distribution. FID is the free induction decay, $\pi$ and $\pi/2$ are the 180 and 90 degrees pulses, TE is the echo spacing which is the time between two consecutive 180 degrees pulses. Echo train (the dashed line) is the raw data for $T_2$ distribution measurement.

We simulated the effect of signal to noise ratio, echo spacing, smoothing parameter (With software courtesy of Magritek™) by designing $T_2$ distributions and their corresponding echo train data. We modeled various $T_2$ distributions by changing the number and the relaxation rate of the $T_2$ peaks. We used the non-negative least square (NNLS) inversion to invert the echo train data to produce the $T_2$ distribution. The simulation software allowed us to create uni- and bi-modal $T_2$ distributions at different relaxation rates and study the effect of acquisition parameters on the $T_2$ distributions inverted from echo train data.

Figure 7A:
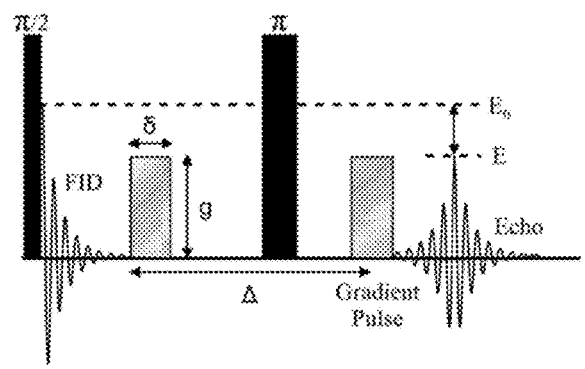
FIGS. 7a-b illustrate schematics of the PFG and PFG-CPMG pulse sequences.

Self-diffusion (henceforth referred as diffusion) is a random translational motion of the molecules which is driven by internal kinetic energy (Price, 1997). We will limit our analysis to the hydrogen nuclei that is most important for NMR applications in oil and gas industry. Diffusion measurements using pulsed filed gradient (PFG) (FIG. 7a), stimulated pulse field gradient (PFGST) (Tanner, 1970) and diffusion editing (Hürlimann et al., 2002) have been used to identify fluid saturations (Freedman et al., 2002, Hürlimann et al., 2002,) and characterize the pore structure in reservoir rocks (Mitra and Sen, 1992, Latour et al., 1995, Hürlimann et al., 2002, Pape et al., 2006). The diffusion coefficient is calculated using Equation 1 (Stejskal and Tanner, 1965) and is proportional to the attenuation of magnetization from FID to the first echo (FIG. 7a).

$$\ln\left(\frac{E}{E_0}\right) = -D\delta^2\gamma^2 g^2\left(\Delta - \frac{\delta}{3}\right) \quad \text{Equation 1}$$

Where $E_0$ and E are the magnetizations of the FID and spin echo (FIG. 7a), respectively, D is the diffusion coefficient, $\delta$ is the gradient pulse duration, $\gamma$ is the magneto gyric ratio of the spins ($2.675\times10^{-8}$ rad s$^{-1}$ T$^{-1}$ for hydrogen nuclei), g is the gradient pulse amplitude, $\Delta$ is the time duration between the gradient pulses (diffusion time).

In wireline logging, diffusion measurements are combined with CPMG measurements (FIG. 7b) to produce a 2d map of fluid diffusivity and transverse relaxation (D-$T_2$ maps) (Sun and Dunn, 2005, Toumelin et al., 2006). This pulse sequence combines two phenomena: the $T_2$ distributions and the translational diffusion coefficients of the fluid molecules. The chemical properties of water and oil are captured in the 1d $T_2$ distributions while the diffusion coefficient measures the reduction in the bulk diffusion coefficient of the fluid due to restrictions of the molecules by the pore walls (Hürlimann and Venkataramanan, 2002). The D-T maps are produced with a two dimensional inverse Laplace transform (Hürlimann et al, 2002, Venkataramanan et al., 2002, Aichele et al., 2007; Song, 2010).

Figure 7B:
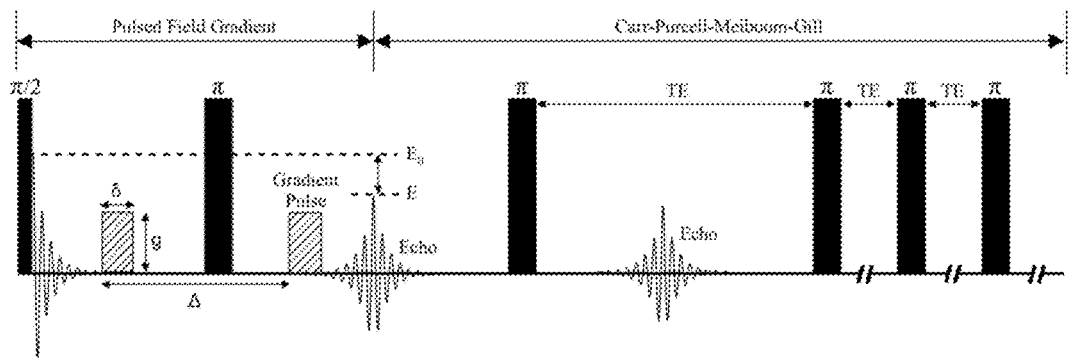

FIG. 7: Schematic of the (FIG. 8a) PFG and (FIG. 7b) PFG-CPMG pulse sequences. Diffusion coefficient can be measured using PFG (FIG. 7a) pulse sequence and when combined with CPMG (FIG. 7b) it can be utilized for fluid typing and saturation calculation. $\pi$ and $\pi/2$ are the 180 and 90 degrees pulses, $\Delta$ is the diffusion time which is the time between gradient pulses, $\delta$ is the gradient pulse duration, g is the gradient pulse amplitude, TE is the echo spacing which is the time between two consecutive 180 degrees pulses.

For comparison, we also modeled spin echo attenuations due to translational spin diffusion with two analytical solutions of the Bloch equations for idealized spherical pore geometries: Gaussian Phase Distribution (GPD) and Short Gradient Pulse (SGP) (Bloch, 1946; Torrey, 1956).

GPD assumes that the phase distribution is Gaussian and the attenuation due to translational motion of the spins in a magnetic field gradient can be modeled using Equations 2 to 4 (Murday and Cotts, 1968). The SGP approximation (Equation 5) assumes that the spin motion is negligible in pulse gradient duration and spin diffusion does not occur (Balinov et al., 1993).

$$E(g) = \exp\left(-\frac{2\gamma^2 g^2}{D^2} \times \sum_{n=1}^{\infty} \frac{2\alpha_n^2 D\delta - 2 + 2L(\delta) - L(\Delta - \delta) + 2L(\Delta) - L(\Delta + \delta)}{\alpha_n^6(R^2\alpha_n^2 - 2)}\right) \quad \text{Equation 2}$$

$$L(t) = \exp(-\alpha_n^2 Dt) \quad \text{Equation 3}$$

Where E(g) is the signal attenuation at each gradient step, $\gamma$ is the magnetogyric ratio, g is the gradient amplitude, D is the diffusion coefficient of the fluid, $\delta$ is the gradient pulse length, $\Delta$ is the diffusion time, R is the idealized spherical pore radius and $\alpha_n$'s are the solutions of the Equation 7 (J is the Bessel function of the first kind)

$$(\alpha_n R)J_{3/2}(\alpha_n R) - \frac{1}{2}J_{3/2}(\alpha_n R) = 0 \quad \text{Equation 4}$$

SGP assumes the gradient pulse length is equal to zero and self-diffusion does not occur during the pulsing period. The attenuation can then be modeled as (Balinov et al., 1993).

$$E(g) = \frac{9[q\cos(q) - \sin(q)]^2}{(q)^6} - 6(q)^2 \sum_{n=0}^{\infty} [j'_n(q)]^2 \quad \text{Equation 5}$$

$$\sum_m \frac{(2n+1)\alpha_{nm}^2}{\alpha_{nm}^2 - n^2 - n} \times \exp\left(\frac{\alpha_{nm}^2 D\Delta}{R^2}\right) \frac{1}{[\alpha_{nm}^2 - (\gamma g \delta R)^2]^2}$$

Where q=$\gamma g\delta R$ and $j_n$ is the spherical Bessel function of the first kind $\alpha_{nm}$ is the m$^{th}$ root of the equation $j_n'(\alpha)=0$ and can also be expressed in terms of the Bessel function of the first kind $$nJ_{n+\frac{1}{2}}(\alpha) - \alpha J_{n+\frac{3}{2}}(\alpha) = 0.$$

In the GDP and the SGP models, the spin echo attenuation is a function of pore radius. The rest of parameters are either known or are acquisition parameters specified in the experiment design. We use both models to estimate the spin echo attenuations and the reliability of diffusion measurements in mudrocks.

The raw echo train data and data are registered as voltage decay (in μV) as a function of time (in ms or s). The amplitude decays are results of relaxation of spins in an echo train data or attenuation of spins due to incoherency in a magnetic field gradient. The commonly-used $T_2$ distributions are obtained by mathematically inverting the "most likely" or best representation of the $T_2$ times that would produce the echo train data or the diffusion coefficient that would cause the attenuation (Coates et al., 1999). In this section, we briefly introduce the inversion for $T_2$ distribution; the other measurements including 1 d and 2d maps follow the same mathematical principles.

For simple systems, such as low viscosity bulk fluids, a single exponential function adequately describes the relaxation phenomena in the echo train data. More complex systems, such as fluid-saturated porous media, require a multi-exponential function to model the relaxations creating an ill posed mathematical problem which has a trivial solution (Whittall and MacKay, 1989; Buttler et al., 1981).

Assuming full polarization of all the hydrogens before CPMG sequence, we can present the echo train data in the form of a summation in:

$$g_i = \frac{M(t_i)}{M_0} = \sum_{j=1}^{m} f_j e^{\frac{-t_i}{T_j}} + \epsilon_i \quad i = 1, \dots, n \quad \text{Equation 6}$$

In which $g_i$ is $i^{th}$ echo amplitude, $M(t_i)$ is the magnetization at $t=t_i$, $M_0$, is the magnetization at $t=0$, $f_j$ is the amplitude for each predefined $T_j$, $t_i$ is experiment time, $T_j$ is the predefined relaxation step and $\epsilon_i$ is the error.

Since $f_j$ and $T_j$ are both unknown, nonlinear inversion algorithms use an iterative method to solve for both unknowns simultaneously, requiring initial estimates to start the iteration. This iterative approach imposes limitations on the number of relaxation times to prevent problems such as divergence or convergence to a local minimum (Whittall and MacKay, 1989). In the linear approach, however, we assume a number of $T_j$ values and solve Equation 6 for $f_j$ values by minimizing the error (Dunn et al., 2002).

In Equation 6, the $T_j$'s represent different pore sizes and the $f_j$'s are the volume of the pores (porosity) with characteristic relaxation time (pore size) of $T_j$. Since $f_j$'s are representation of porosity at each $T_j$, the solution to the problem cannot be negative. The problem can be solved using Non Negative Least Square (NNLS) approach proposed by Lawson and Hanson (1974). This approach results in distribution of discrete delta functions, which are sharp spikes at different $T_j$ values. Although this solution minimizes the error in Equation 6, it does not represent the continuous pore size distributions of porous rocks. To impose this criterion, a second constraint of continuity and smoothness of the distribution is imposed on the solution. Both constraints and their implementation to solve the Equation 6 form the basis for various linear inversion algorithms. The general form of the regularized equation is shown in Equation 7.

$$\phi(f) = \frac{1}{2} \sum_{i=1}^{n} \left( \sum_{j=1}^{m} f_j e^{\frac{-t_i}{T_j}} - g_i \right)^2 + \alpha R(f_j) \quad \text{Equation 7}$$

where $R(f_j)$ is the regularization or penalty function and $\alpha$ is the smoothing parameter. Each inversion algorithm uses different regularization functions and requires a different solution.

The right hand side of Equation 7 has two parts. The first part is the conventional least square fitting and the second part is the regularization component. Without regularization, the $T_2$ distributions are modeled as sharp, unstable, and non-reproducible peaks. The smoothing parameter $\alpha$, creates a balance between stability of the produced peaks and over-weighting the regularization function. The right hand side of Equation 7 has two parts. The first part is the conventional least square fitting and the second part is the regularization component. Without regularization, the $T_2$ distributions are modeled as sharp, unstable, and non-reproducible peaks. The smoothing parameter $\alpha$, creates a balance between stability of the produced peaks and over-weighting the regularization function. Indiscriminate increases in $\alpha$ increase the weight of the regularization function and over-smooth the distribution (Casanova et al., 2011). Proposed solutions of this problem, regardless of the inversion type and solution algorithm, should minimize the misfit factor:

$$\chi^2 = \sum_{i=1}^{n} \left( \sum_{j=1}^{m} f_j e^{-t_i/T_j} - g_i \right)^2 \quad \text{Equation 8}$$

Statistically, $\chi^2$ is expected to correspond to the number of echoes in the experiment. The optimal smoothing parameter can be obtained by plotting $\chi^2$ as a function of $\alpha$ (Casanova et al., 2011). Alternatively, the smoothing parameter can be calculated (Dunn et al., 1994). We use the Dunn et al. (1994) approach to calculate the "optimum smoothing parameter"

We now discuss the specific challenges in mudrocks for data acquisition and for choosing appropriate parameters in data inversion. We also investigate the reliability of restricted diffusion in mudrocks by comparing experimental data with analytical models of the diffusion phenomena.

In this study we aim to discuss the most important aspects of NMR data acquisition and analysis in unconventional rocks. In all cases we compare two cases; a sandstone case and a shale case with long and short relaxation times, respectively. We investigate the significance of different parameters on data acquisition and inversion for each case. Both experimental results and simulations are utilized to compare both cases.

NMR data are acquired using pulse sequences. We discuss features of the pulse sequences as well as instrument limitations that might prevent high resolution data acquisition in mudrocks.

Echo Spacing (TE)

Echo spacings (TE) specify the timing of the 180° pulses as well as initiation of spin echo amplitude data acquisition. Minimizing TE in the CPMG sequence can improve the NMR signal by allows acquisition of fast relaxing components and by diminishing diffusion effects.

Figure 8A:
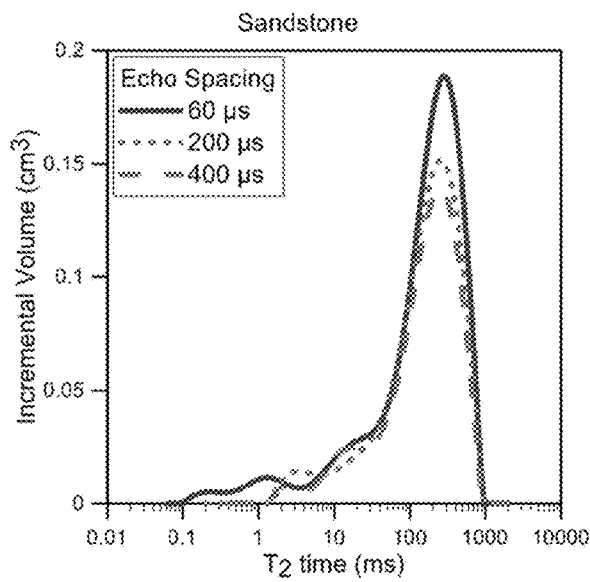
FIGS. 8a-b illustrate $T_2$ distributions measured with TE of 60 μsec, 200 μsec and 400 μsec.
Figure 8B:
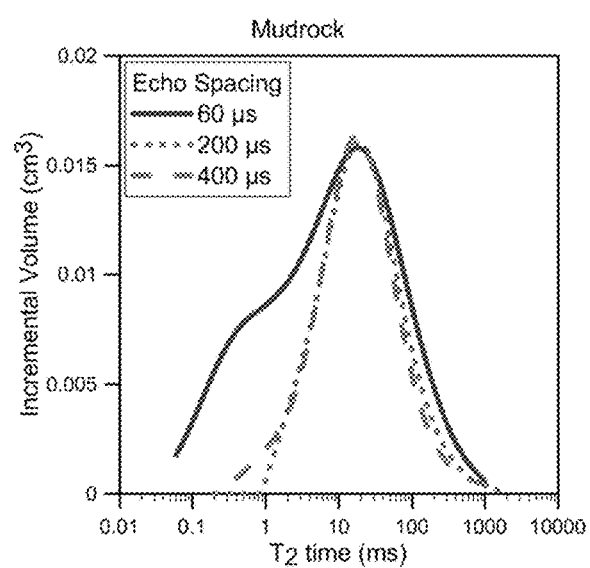

The sooner the acquisition starts, the more spin echoes are detected, and the higher the signal to noise ratio achieved (Coates et al., 1999). Furthermore, the early time signals, significant in samples with fast relaxing hydrogens, such as heavy oils and mudrocks, can be captured. In FIG. 8, we compare the effect of echo spacing on capturing the fast relaxing components of a sandstone (FIG. 8a) and a mudrock (FIG. 8b). The echo train acquired with a TE=60 μs shows a peak at 0.4 ms which is diminished when the TE is increased 200 and 400 μs. The increased TE had negligible effect on the $T_2$ distributions of the high porosity sandstone (FIG. 8a) since the short relaxation times represent less than 3% of the total porosity. In the low porosity mudrock however, larger TE fail to measure spins that generate the 0.4 ms peak because they decay before the acquisition starts. These spins account for more than 34% of the total porosity.

Spin diffusion in pore space due to magnetic field inhomogeneity and presence of internal gradients imposes an additional spin relaxation; the diffusion induced relaxation (Hürlimann, 1998). Since performing the experiment without magnetic gradients is practically impossible, minimizing TE can reduce diffusion induced relaxations (Saidian et al., 2015a). At low frequencies (2 MHz), the diffusion induced relaxation in negligible in mudrocks due to their small pore sizes regardless of the diffusion coefficient variations of the saturating fluids or the magnetic susceptibility variations in the pore space (Washburn, 2014). Consequently, the relaxation peak at 10 ms in the mudrock does not change with increased TE (FIG. 8a). However, the sandstone (FIG. 8b) shows significant diffusion effects; at TE=400 μs, the peak amplitude around 200 ms reduced by 5% of the total porosity.

FIG. 8: $T_2$ distribution measured with TE of 60 μsec, 200 μsec and 400 μsec for (FIG. 8a) sandstone and (FIG. 8b) mudrock samples. Acquiring data with longer TE disregards the fast relaxing components in the $T_2$ distribution for mudrocks (FIG. 8a). Long TE also increases the diffusion effect by imposing an extra relaxation and reduces the peak amplitude for sandstone (FIG. 8b).

Variations in the duration, amplitude and frequency of RF pulses due to practical limitations compromise the data acquisition timing of the NMR signal. Several delay times are associated with both transmitting the pulse and acquiring the NMR signal: free ringing, damping and group delays. We briefly discuss the definition, source and the effect of each delay on acquisition of the NMR signal (Mitchell et al., 2014).

Ideally, the probe should recover immediately after transmitting the rf pulse and start acquiring data. However, the energy in the rf pulser coil does not dissipate instantly and leads to acoustic ringing (Buess and Petersen, 1978; Peshkovsky et al., 2005). The induced rf signal in the coil caused by excitation of internal metallic parts of the probe due to initial pulsing is called acoustic ringing (Morris and Toohey, 1985); it can last up to several milliseconds depending on the magnet strength and quality factor and the pulse frequency (Buess and Petersen, 1978). Acoustic ringing interferes with NMR signals from the sample as its frequency overlaps with the RF pulse and the Larmor frequency. Ringing effects can be eliminated by simply delaying acquisition until the ringing decays. A damping pulse can expedite the ringing decay process. However, since the damping pulse might create free ringing as well, an additional damping delay is required to eliminate that ringing as well. The time required for the probe to recover from the various free ringing is called the "ringing and damping delay" or "probe dead time" (Mitchell et al., 2014).

The NMR signal is digitally filtered to improve signal to noise ratio (SNR) (Moskau, 2001). Both, the rf pulse transmitted by the probe and the signal received from the sample are filtered to narrow the frequency range and improve data quality. Each filtering process imposes a filtering time delay, known as "group delay".

Figure 9A:
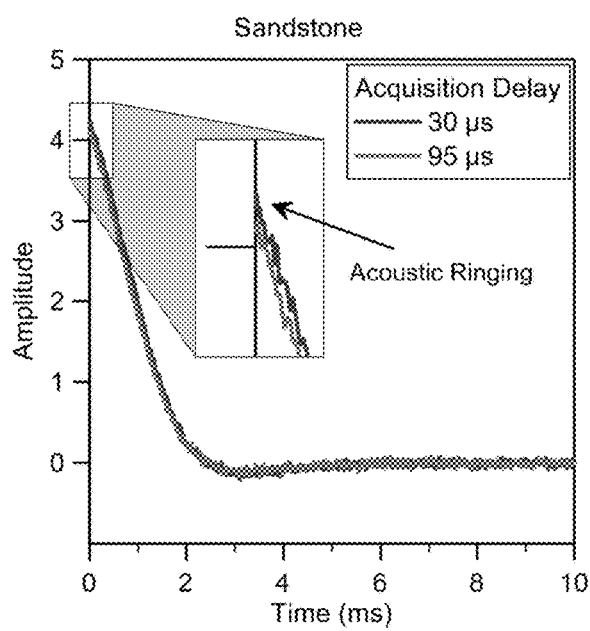
FIGS. 9a-b illustrate FID signals for a mudrock sample.
Figure 9B:
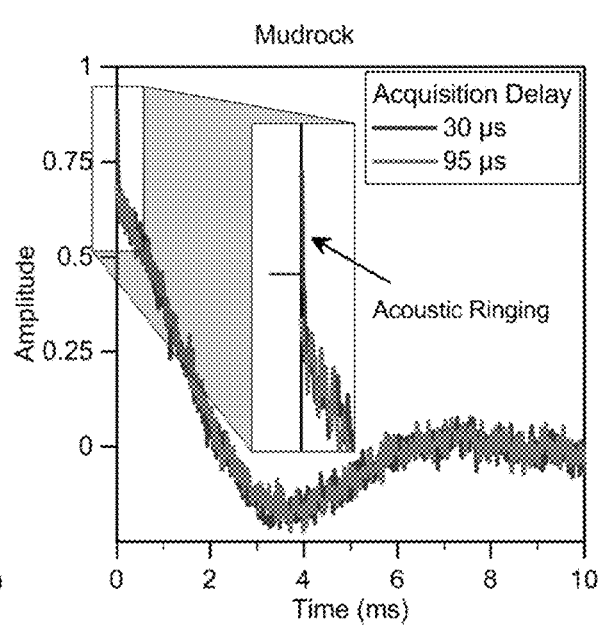

The group delays and the probe dead time together determine when signal acquisition from the sample can start; it is the minimum practical TE of an NMR instrument. Although, minimizing the TE is desirable in samples with fast relaxing hydrogen nuclei, choosing too small a delay time to achieve minimum TE results in appearance of unwanted signals such as ringing effect. The interference from these unwanted signals is significant in mudrocks where the actual signal is weak due to low porosity or decay of fast relaxing hydrogens during the delay times. FIG. 9 shows the effect of variation of total delay on the acquired FID signal for a mudrock and a sandstone. At low acquisition delay (30 μs), the interference from free ringing for both samples is captured by the receiver. The acoustic ringing amplitude is negligible for the sandstone with a high NMR signal (FIG. 9a). On the other hand, for the mudrock (FIG. 9b), the acoustic ringing is as high as 25% of the actual signal from the sample. This extra amplitude can be interpreted as the signal and, if not accounted for, result in overestimation of porosity and micropore volume. An acquisition delay larger than 90 μs eliminates acoustic ringing for both samples (FIG. 9).

FIG. 9: FID signal for a mudrock sample with (FIG. 9a) 30 μsec and (FIG. 9b) 95 μsec delays (damping and acquisition delay combined). The probe acoustic ringing is shown by the circle in figure (FIG. 9a) for short delay. At low acquisition delay (30 μs) the acoustic ringing for both samples is captured by the receiver. For the sandstone (FIG. 9a) the acoustic ringing amplitude is negligible whereas for the mudrock (FIG. 9b) the acoustic ringing is about 25% of the signal. Increasing the acquisition delay to 90 μs eliminates the acoustic ringing for both samples.

Figure 10A:
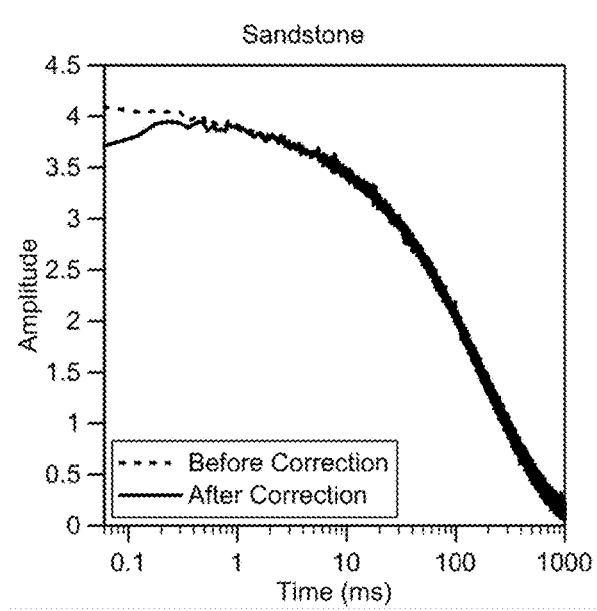
FIGS. 10a-b illustrate original and background subtracted echo train data for sandstone and mudrock samples.
Figure 10B:
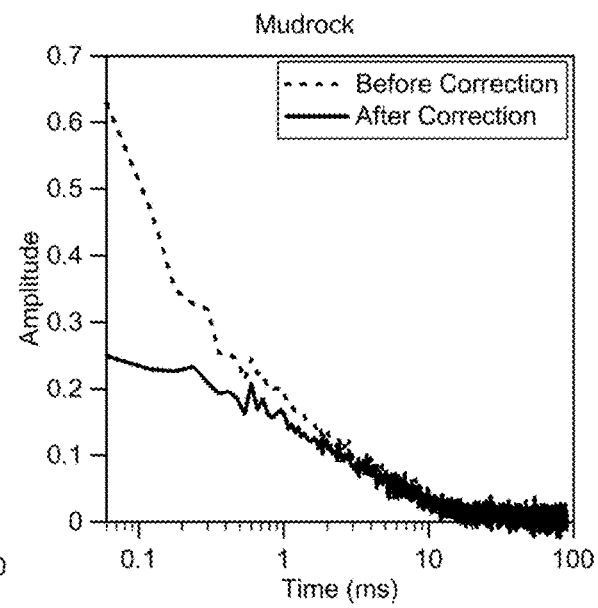
Figure 11A:
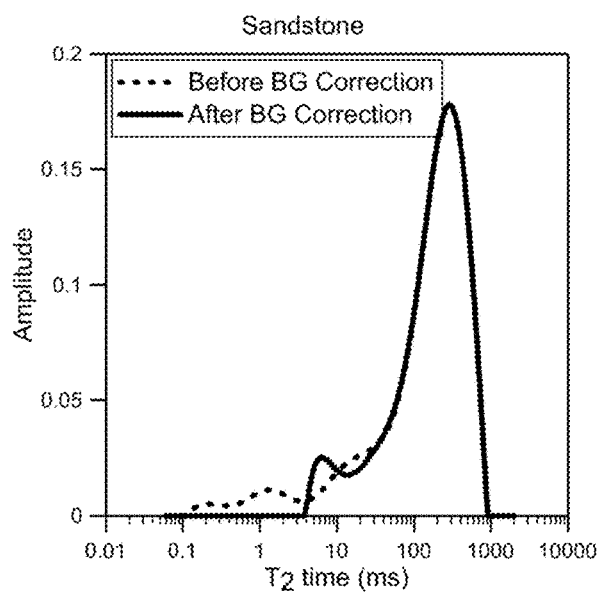
FIGS. 11a-b illustrate $T_2$ distributions for before and after background subtraction for sandstone and mudrock samples.
Figure 11B:
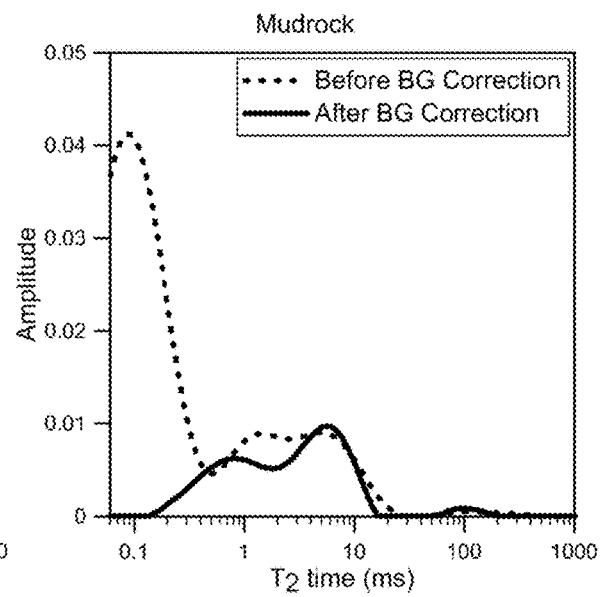

Low field NMR signals originate from hydrogen nuclei in the sample. Hydrogen atom contamination in the test environment, e.g. from sample containers, plastic or Teflon wraps and ambient moisture, might also produce a detectable signal. A common practice is to capture the background signal by repeating the same experiment on the sample container and wraps without the sample and subtracting the background noise from the original signal. To avoid adding noise to the data, the SNR of the background signal must match or exceed that of the sample. In high porosity rocks, with high amplitude NMR signals, background noise is negligible compared to the main signal. In low porosity rocks, contribution from the background noise is significant and can be interpreted as real signal and lead to overestimation of porosity and micro-pore volume. FIG. 10 displays the NMR signal and FIG. 11 shows the $T_2$ distributions before and after background removal for a high porosity sandstone (FIG. 10a; FIG. 11a) and a low porosity mudrock (FIG. 10b; FIG. 11b). Note that the change in the signal amplitude at early times for the mudrock sample is significant (up to 60% of the total porosity), whereas it is smaller for the sand sample (less than 6% of the total porosity).

FIG. 10: Original and background subtracted echo train data for (FIG. 10a) Sandstone and (FIG. 10b) Mudrock sample. As shown the background signal amplitude is negligible for Sandstone sample but it changes the Mudrock signal significantly after subtraction.

FIG. 11: $T_2$ distributions for before and after background subtraction for (FIG. 11a) Sandstone and (FIG. 11b) Mudrock samples. The changes in Sandstone spectrum are negligible but for the mudrock a major part of the fast relaxing components have been removed.

Depending on the sample properties, such as fluid viscosity or pore size distribution of the rock, the time required for the echo train to decay to noise level varies. Enough echoes for a specific TE value are required to capture all different hydrogen nuclei with different relaxation rates. FIG. 12 shows that the echo train decays are different in a sandstone and a mudrock sample although both samples are saturated with the same fluid. Due to differences in the pore structure and mineralogy, hydrogen nuclei in the mudrock sample relax faster than in the sandstone. At any given TE time, it is best practice to increase the number of echoes until the echo train data decays to noise level. Similar to acquiring data with long TE which discounts fast relaxing components, acquiring data with insufficient number of echoes leads to discounting slow relaxing hydrogen and incomplete $T_2$ distribution.

Figures 12A, 12B:
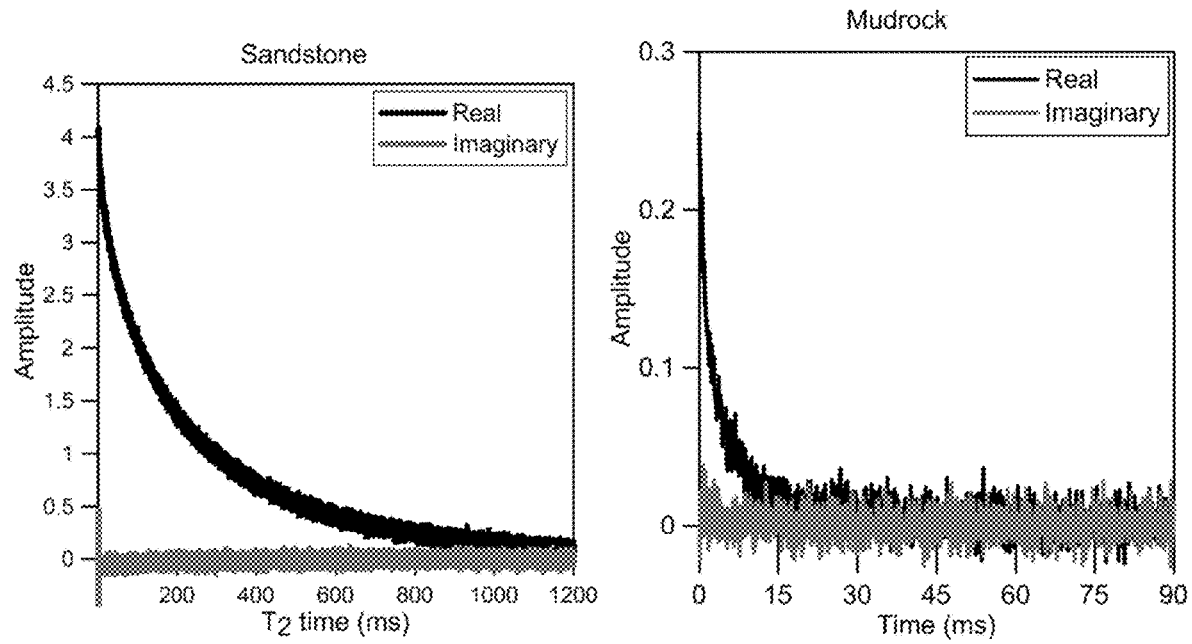
FIGS. 12a-b illustrate the echo train data acquired with 60 μsec TE for sandstone and mudrock.

FIG. 12: The echo train data acquired with 60 μsec TE for (FIG. 12a) Sandstone and (FIG. 12b) Mudrock. As we see in both figures the echo train amplitude (solid black line) reaches to noise level (light gray line) at the end of the experiment.

Appropriate mathematical inversion is required for accurate analysis and interpretation of NMR data, regardless of SNR and data quality. The reliability of any inversion can be compromised by acquisition parameters, sample properties and instrument limitations. We discuss here the factors that affect the inversion process, such as smoothing, SNR and relaxation rate.

Figure 13:
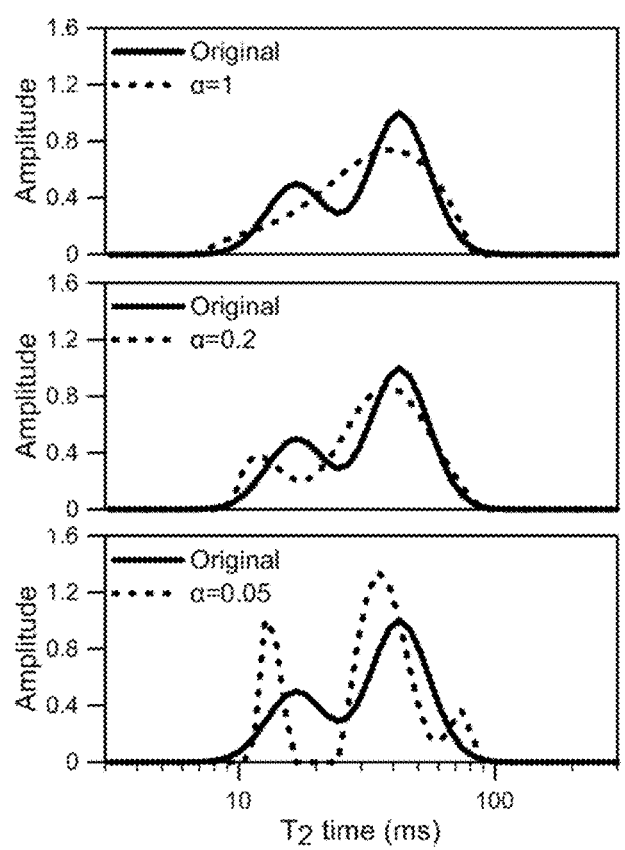
FIG. 13 illustrates the effect of smoothing parameter on the inversion result.

We use the regularization function to produce a smooth $T_2$ distribution to represent the pore size distribution of a natural rock. The smoothing parameter (α in Equation 7) is the regularization weight; it plays a significant role in the $T_2$ distribution shape. Without regularization, the inversion produces discrete delta functions. FIG. 13 shows the original $T_2$ distribution used to produce the echo train data and the inversion results with different smoothing parameters. is also shown for comparison. Decreasing the smoothing parameter from 1 to 0.05 (FIGS. 13a to 13c) changes the distribution from a broad single peak biased by the regularization function (FIG. 13a) to sharp and discrete peaks which are similar to discrete delta functions (FIG. 13c). The optimum smoothing parameter is the compromise between instability of the delta-type result and bias by over-smoothing. In the following section, we discuss how SNR and relaxation rate affect the smoothing parameter value.

FIG. 13: Effect of smoothing parameter on the inversion result. Smaller smoothing parameters lead to sharp and thin peaks in the $T_2$ distribution, while larger smoothing parameters broaden the spectrum and combine the peaks in the original spectrum to one broad peak.

Figure 14A:
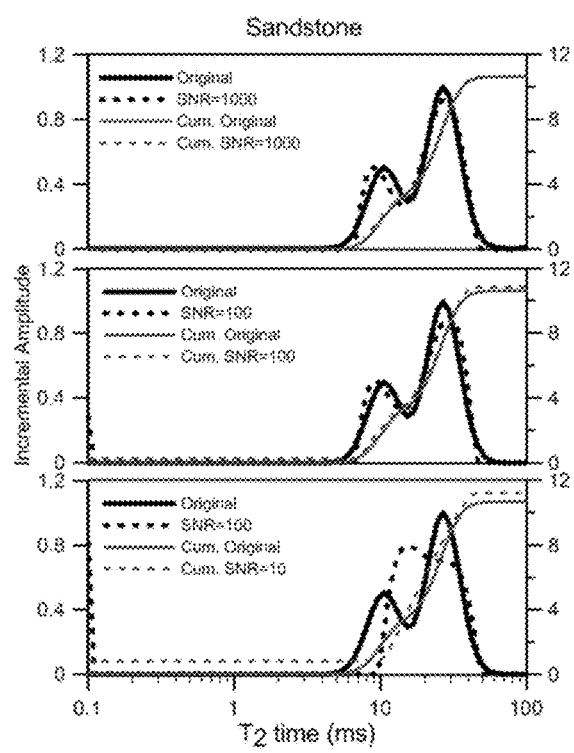
FIGS. 14a-b illustrate a comparison of a synthetic $T_2$ distribution for sandstone and mudrock.
Figure 14B:
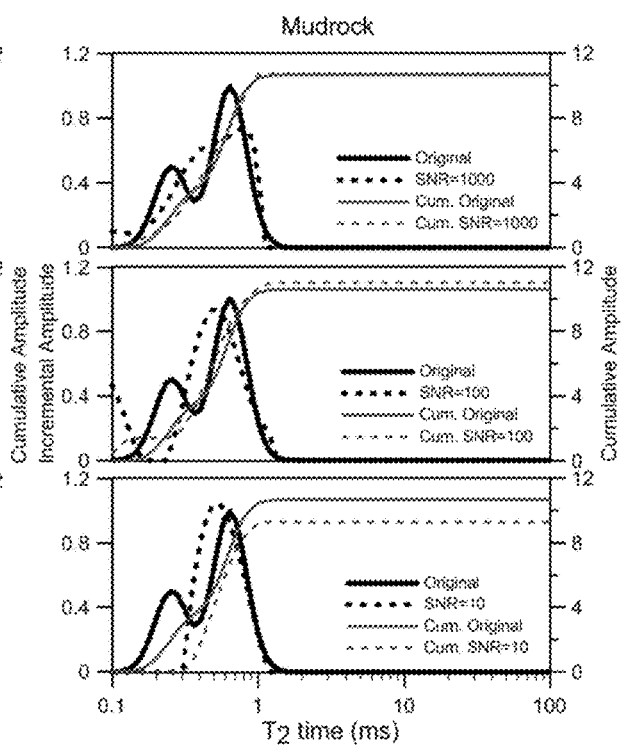

Signal to noise ratio (SNR) is a measure of the quality of the NMR data. It is the ratio of the initial magnetization amplitude in echo train data to the average noise amplitude. Doubling the number of experiments (NMR scans) increases the SNR by a factor of $\sqrt{2}$. We simulated synthetic $T_2$ distributions with similar shapes, TEs and number of echoes but with variable relaxation rates and SNR. The mudrock and the sandstone spectra can be differentiated by fast (FIG. 14a) and slow (FIG. 14a) relaxation rates, respectively. We inverted the echo train data using various smoothing parameters to reproduce either the original spectrum (solid curves in FIG. 14) or the spectrum with most similarity to the original spectrum. FIG. 14 shows that (a) for sandstone (FIG. 14a), the original spectrum is reproduced for high SNR scenarios (>>10 SNR). (FIG. 14b) For mudrock sample (FIG. 14b), the original spectrum was not recovered even at the high SNR of 1000. (c) All the inverted spectra for the mudrock are unimodal. (d) Lower SNR (<10) signals yield inversion artifacts at fast relaxing times that might be interpreted as micro porosity. (e) The total amplitude calculated from $T_2$ distributions remained unaffected by the SNR values. Our simulation results show that for fast relaxing samples such as mudrocks, regardless of the quality of the data, the original $T_2$ distribution cannot be reproduced by the inversion process. Also the inverted $T_2$ distribution does not show the bimodal or multi-modal distribution of the pore structure in mudrocks and inversion artifacts appeared at short relaxation times might be interpreted as micro-porosity.

To investigate why the inversions failed to reproduce the $T_2$ spectrum for the mudrock (FIG. 14b), we simulated synthetic echo train data for a fast and a slow relaxing scenario each with a uni- and a bi-modal spectrum. The TE, number of echoes and SNR were kept constant. The smoothing parameter used to simulate the original $T_2$ distribution is denoted as "simulated smoothing parameter," while the smoothing parameter calculated using the method of Dunn et al. (1994) is denoted as "optimum smoothing parameter".

FIG. 14: Comparison of a synthetic $T_2$ distribution for (FIG. 14a) Sandstone and (FIG. 14b) Mudrock. The original $T_2$ spectra are shown as solid curves and the inverted spectra are shown as dashed curves. For the sandstone (FIG. 14a) the original shape of the $T_2$ distribution is reproduced by inversion. But for the mudrock, due to fast relaxation and proximity of two peaks, even at SNR of 1000 the original shape of the $T_2$ distribution is not reproduced.

Figure 15:
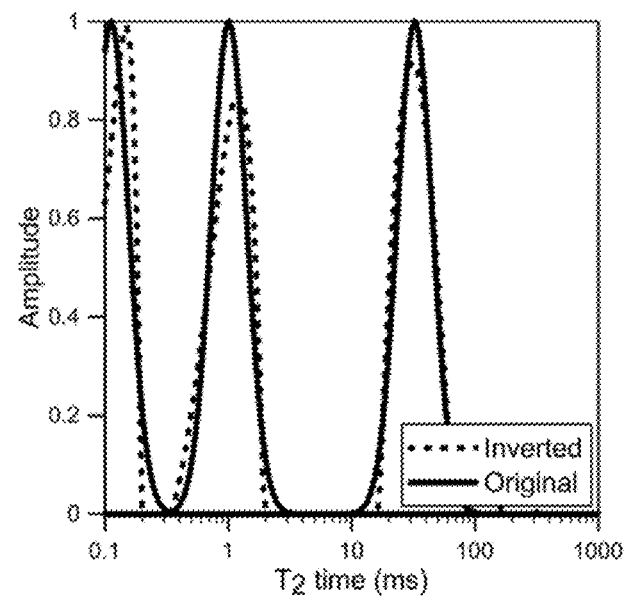
FIG. 15 illustrates original and inverted $T_2$ spectra for single peak distributions at three different relaxation rates.
Figure 16:
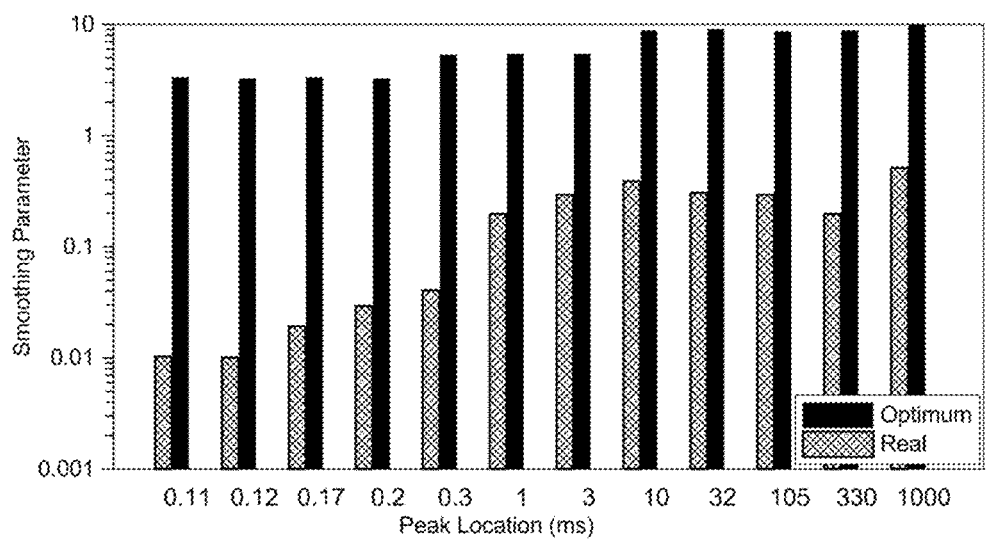
FIG. 16 illustrates a comparison of real and optimum smoothing.

FIG. 15: Original and inverted $T_2$ spectra for single peak distributions at three different relaxation rates. In this figure only the results of inversion using real smoothing parameter are shown. As it is shown all the peaks regardless of the relaxation rates are reproduced by inversion. FIG. 15 shows both original and inverted $T_2$ spectra for unimodal distributions at three different relaxation rates calculated using the simulated smoothing parameter. All the peaks, regardless of the relaxation rates, were reproduced by inversion. Comparison of real and optimum smoothing for in FIG. 16 shows that the optimum smoothing parameter is up to 3 orders of magnitude higher than real smoothing parameter. The difference is larger for faster relaxation peaks. Increasing the relaxation rate at a constant TE time reduces the number of data points in the echo train data. Consequently, the inversion algorithm uses a limited number of points to reproduce the distributions. In this case, higher smoothing parameter is calculated to increase the weight of the regularization function and the resulting distribution is biased by this function.

FIG. 16: Comparison of real and optimum smoothing in shows that the optimum smoothing parameter is systematically higher than real smoothing parameter up to 3 orders of magnitude. The difference is higher for faster relaxation peaks.

Figure 17:
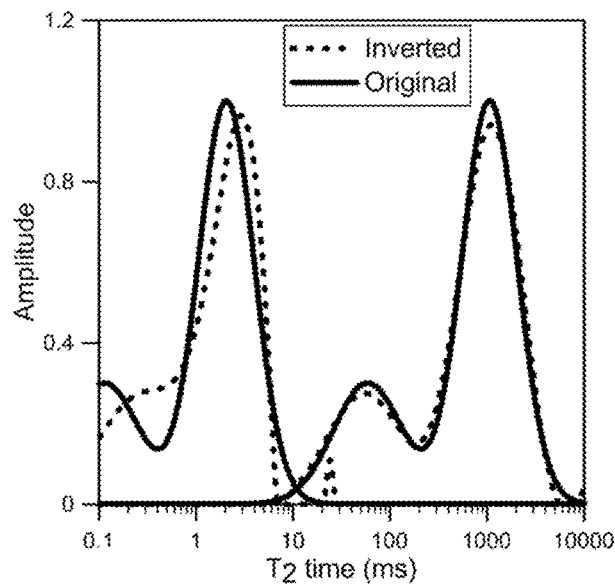
FIG. 17 illustrates original and inverted $T_2$ spectra for double peak distributions at two different relaxation rates.

FIG. 17 shows the results for the simulation of bimodal distributions for two different samples with high and low relaxation rates. The inversion successfully reproduced both peaks of the spectrum with low relaxation rate; in the fast relaxation spectrum, the peaks are not accurately resolved after inversion. Similar to the unimodal scenario (FIG. 16), the simulated smoothing parameter is smaller than optimum smoothing parameter (FIG. 18), and this difference increases with increasing relaxation rate.

FIG. 17: Original and inverted $T_2$ spectra for double peak distributions at two different relaxation rates. In this figure only the results of inversion using real smoothing parameter are shown. The inversion process gave a mismatch for fast relaxation peak.

Figure 18:
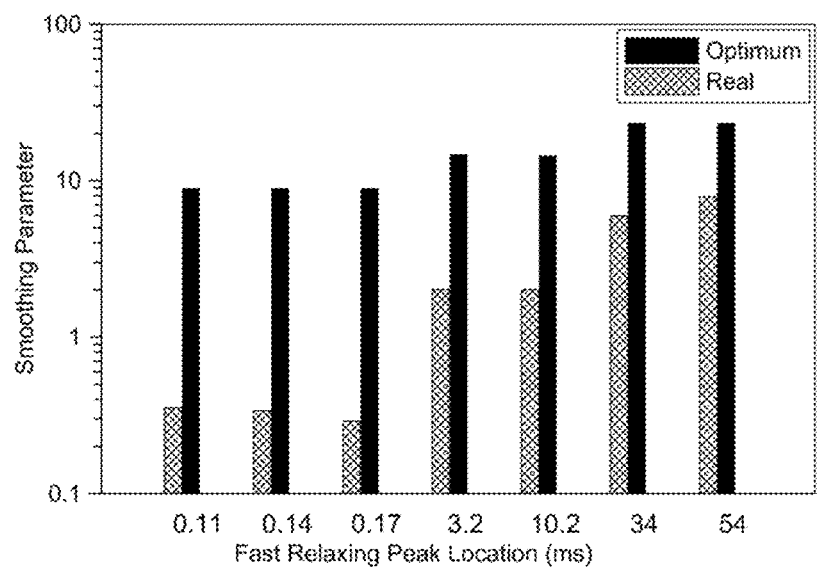
FIG. 18 illustrates a comparison of real and optimum smoothing parameter.

FIG. 18: Comparison of real and optimum smoothing parameter. It shows that the optimum smoothing parameter is systematically higher than real smoothing parameter up to 3 orders of magnitude. The difference is higher for faster relaxation peaks.

The results of simulation shows that for mudrocks using the optimum smoothing parameter results in a broad distribution due to over-smoothing the spectrum. Multi-modal distribution is an indication of presence of different pore sizes or fluids with different viscosities in the rock. Over-smoothing of the distribution masks the $T_2$ spectra by broadening and combining the peaks and hinders the proper interpretation the NMR $T_2$ distributions.

Restricted diffusion measurements presented as 2d D-T maps, are commonly used for pore characterization, fluid typing, saturation and viscosity determination. There are two main challenges associated with restricted diffusion measurement in mudrocks: the gradient pulse amplitude and the diffusion timing. In this section we discuss these two challenges and the reliability of diffusion measurements in mudrocks by simulating the restricted diffusion phenomena in spherical pores utilizing GPD and SGP models and experimental data for a mudrock sample.

Diffusion measurements are based on the attenuation of the spin echo in a magnetic gradient (the reduction of the magnetization from $E_0$ to E in FIGS. 7a-b). This attenuation is the result of change is spin phases and Brownian motion of the spins in the porous media. The phase change of the spins is a function of the spin location in the magnetic field. Significant phase change or translational motion of the spins in the pores is required for the signal attenuation to be detectable by an NMR instrument. The translational motion of the spins in mudrocks is limited because of the abundance of nano and micro-scale pores in these rocks, so the gradient amplitude has to be strong enough to create a detectable phase change across a single pore.

Figure 19A:
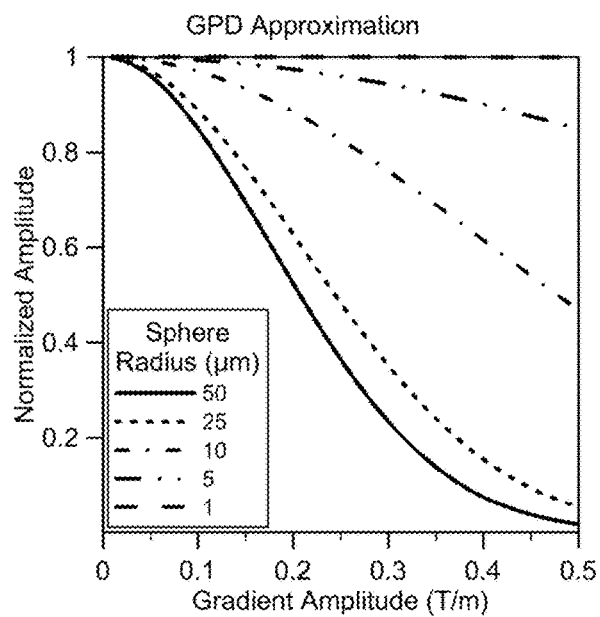
FIGS. 19a-b illustrate the simulation results of signal simulation in spheres with various radii as a result of diffusion of the fluid assuming Gaussian phase distribution.
Figure 19B:
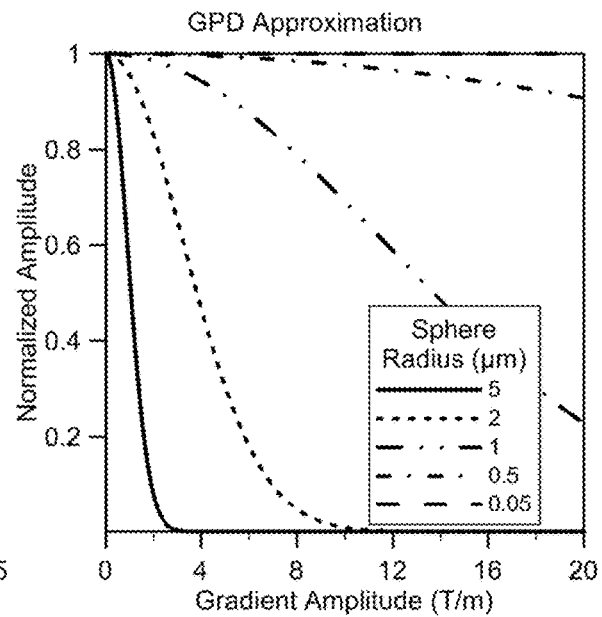
Figure 20A:
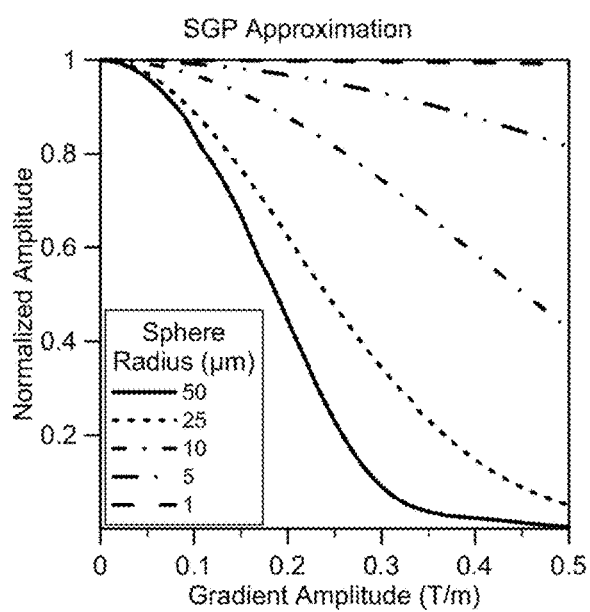
FIGS. 20a-b illustrate the simulation results of signal simulation in spheres with various radii as a result of diffusion of the fluid assuming short gradient pulse.
Figure 20B:
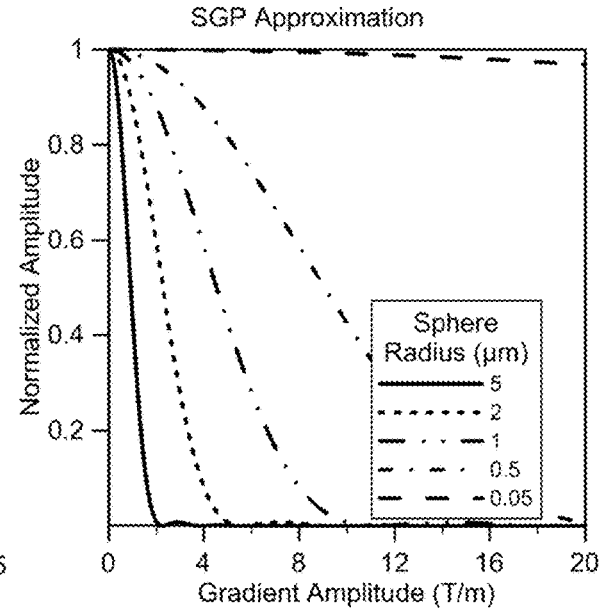

We simulated the spin echo attenuation in a spherical pore using GPD (FIG. 19) and SGP (FIG. 20) models with a fluid diffusion coefficient of 2.5 m²/s, gradient pulse duration of 1.5 ms and diffusion time of 50 ms. We varied the pore radii from 1 to 50 μm for the pulse gradient amplitude of 0 to 0.5 T/m to model low frequency NMR experiments (FIG. 19a and FIG. 20a). We also varied the pore radii from 0.05 to 5 μm for the gradient pulse amplitude of 0 to 20 T/m to model a high frequency NMR experiments (FIG. 19b and FIG. 20b). Common practice for a reliable diffusion measurement is more than 90% signal loss due to diffusion (Bruker™ Diffusion NMR Manual, 2009). Our simulations show that although the SGP model demonstrates higher attenuation for the same acquisition parameters, both models confirm that the attenuation is negligible for 1 μm radius at gradient pulse amplitude of 0.5 T/m (FIG. 19a and FIG. 20a). Also the attenuation for pore radii of 5 and 10 μm was not high enough for a reliable diffusion measurement at this gradient pulse amplitude (FIG. 19a and FIG. 20a). Simulations of signal attenuation at gradient pulse amplitudes up to 20 T/m (FIG. 19b and FIG. 20b) indicated significant attenuation for pores larger than 1 μm radius for GPD model (FIG. 19b) and larger than 500 nm for SGP model (FIG. 20b). Since downhole and low field NMR instruments are limited to gradients below 0.5 T/m, the measured diffusion coefficient is only sensitive to the large pores where the majority of the attenuation occurs.

FIG. 19: The simulation results of signal simulation in spheres with various radii as a result of diffusion of the fluid assuming Gaussian phase distribution (GPD) of the spins for gradient amplitude of (FIG. 19a) 0 to 0.5 T/m and (FIG. 19b) 0 to 20 T/m. The fluid diffusion coefficient is 2.5 m²/s, gradient pulse duration and diffusion times are 1.5 and 50 ms, respectively.

FIG. 20: The simulation results of signal simulation in spheres with various radii as a result of diffusion of the fluid assuming short gradient pulse (SGP) duration for gradient amplitude of (FIG. 20a) 0 to 0.5 T/m and (FIG. 20b) 0 to 20 T/m. The fluid diffusion coefficient is 2.5 m²/s, gradient pulse duration and diffusion times are 1.5 and 50 ms, respectively.

Figure 21A:
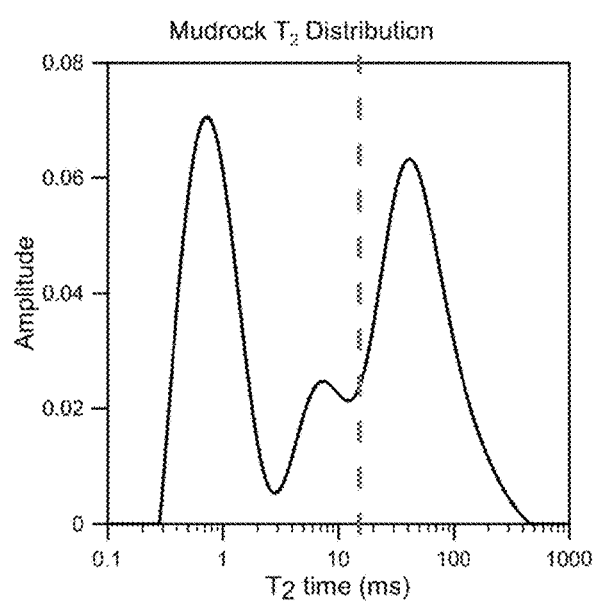
FIGS. 21a-b illustrate a $T_2$ distribution and D-$T_2$ for a mudrock sample.

Diffusion time ($\Delta$ in FIG. 7) is the delay time between two gradient pulses. The translational diffusive motion of the spins during this time period imposes the required signal attenuation for diffusion measurements. A similar phenomenon to acoustic ringing happens is the probe when the gradient pulses are applied. This phenomenon is denoted as eddy current which takes place in different metallic parts of the probe. The eddy currents create gradient artifacts which vary in amplitude depending on the direction of the applied gradient pulse (Chan et al., 2014). The eddy current's effect on NMR signal can be minimized by applying the gradient pulses with a finite ramp time (the time required for the pulse to reach its maximum amplitude) and extending the data acquisition until the eddy currents are decayed (stabilization delay). The minimum diffusion time for a reliable PFG pulsing is determined by the ramp times, stabilization delays and minimum time required for spins to diffuse in the porous media. Typically, in low field NMR measurements, the diffusion time is commonly higher than 10 ms. Relaxation of the spins during diffusion time rules out the contribution of these spins in diffusion measurement. The signal loss due to relaxation before data acquisition for sandstones (FIG. 12a) is less than 10% of the total signal whereas in mudrocks (FIG. 12b) is more than 90% of the total signal. To show the effect of diffusion time on diffusion measurement we compared the $T_2$ distribution and D-$T_2$ map for a mudrock sample (FIG. 21). The D-$T_2$ maps is acquired with diffusion time of 13 ms and maximum gradient amplitude of 0.5 T/m. $T_2$ spectrum showed bimodal distribution with dominant peaks at at 0.8 and 60 ms (FIG. 21a). The signal on the left side of dashed red line in FIG. 21a is not captured in D-$T_2$ map and the $T_2$ distribution measured by the D-$T_2$ pulse sequence shows only the 60 ms peak. The fast relaxing spins (0.8 ms peak) were relaxed during the diffusion time.

Figure 21B:
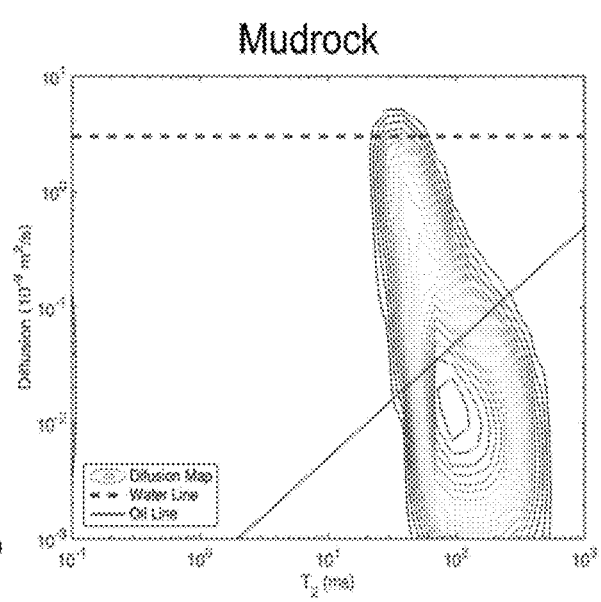

FIG. 21a is $T_2$ distribution and FIG. 21b is a D-$T_2$ for a mudrock sample. The signal on the left side of dashed line in is not captured in D-$T_2$ map due to signal decay during diffusion time. The $T_2$ distribution (FIG. 21a) shows a bimodal distribution but the D-$T_2$ map (FIG. 21b) does not show the peak at faster times. All the spins with relaxation faster than the red dashed line relaxation time decayed in the D-$T_2$ experiment before the data acquisition started.

Tight, low-porosity rocks (also called shales or mudrocks) present unique challenges in NMR data acquisition and signal processing. We have presented errors and pitfalls in NMR experimental design and data processing for such rocks. Thus, Data acquisition should prevent signal interferences from rf pulses and increase NMR data quality by eliminating signals not originating from the sample. Left uncorrected, these interferences and unwanted signals can be interpreted as microporosity in mudrocks. Inversion of NMR data for mudrocks is more challenging than for conventional rocks mainly because of the fast relaxation of the hydrogen nuclei in these rocks. Overestimation of the smoothing parameter, peak broadening and lack of resolution to identify bi or multi-modal distributions are consequences of fast relaxing signal in mudrocks. These effects can lead to over interpretation of the T2 distribution in mudrocks. In the current state of logging technology, downhole restricted diffusion experiments are not reliable for fluid typing and saturation measurements in mudrocks: The pulse gradient amplitude for low frequency instruments is not high enough, and the signal decays significantly due to relaxation of the spins before the acquisition of the spin echo starts.

This study provides insight about NMR data acquisition and signal processing challenges in mudrocks. It highlights the necessary precautions for acquiring NMR data. It also indicates how the rock and fluid properties in mudrocks might compromise the data quality and reliability.

NMR $T_2$ Simulation

Three NMR relaxation mechanisms (surface relaxation, bulk relaxation, and relaxation due to diffusion) have been modeled separately and simultaneously to produce the echo train data in 3D rock models. Bulk relaxation has been modeled by assuming a single exponential decay. Relaxation due to diffusion has been modeled using the diffusion kernel.

Surface relaxation has been modeled by random walk simulation, which simulates the Brownian motion of diffusing particle called random walkers. Walkers move a certain distance at each time step and depending on their new location in the pore space, they might hit the pore wall or move inside the pore body. The walkers that hit the wall might decay or survive, depending on the surface relaxation assigned to the model. The overall live walkers in the pore space at the end of each time step is considered as the magnetization of the model. Information about the walker simulation can be found in Talabi, O. A., 2008, Pore-Scale Simulation of NMR Response in Porous Media, Doctor of Philosophy Thesis, Earth Science and Engineering, Imperial College, London (2008), which is incorporated by reference in its entirety.

Pore Size Measurement

In some embodiments, the measured pore size distribution in a reservoir can be determined using methods known in the art or methods described herein. The measured pore size distribution can be compared to the calculated pore size distribution to calculate adjustment factors for future use.

Surface Relaxivity

The surface relaxivity can be calculated using bulk fluid or image resolution size with NMR. It is a matching method. The surface relaxivity is changed until there is a match of the calculated pore size distribution with the measured pore size distributions. The bulk relaxation can vary. The diffusion coefficient varies. The image resolution varies. The simulation fluid can be selected from the group consisting of deionized water, or other known fluids or combinations thereof. The resolution of the voxels can vary.

Reservoir and Rock Types

The present invention can be directed several types of reservoirs or rock types, including but not limited to, sandstone and mudrocks.

EXAMPLE 1

Figure 2A:
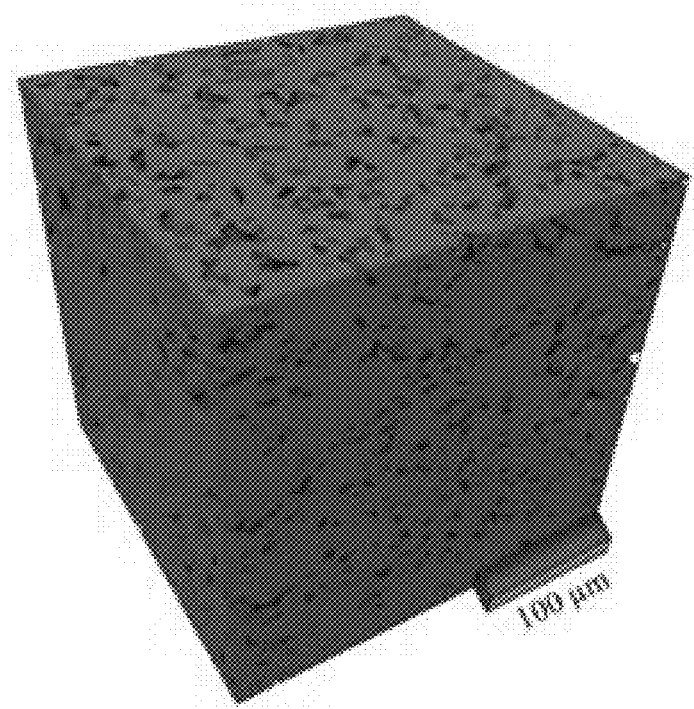
FIG. 2(a) illustrates the constructed rock model with 300 μm×300 μm×300 μm size (1 μm resolution) and 16.86 p.u. porosity.
Figure 2B:
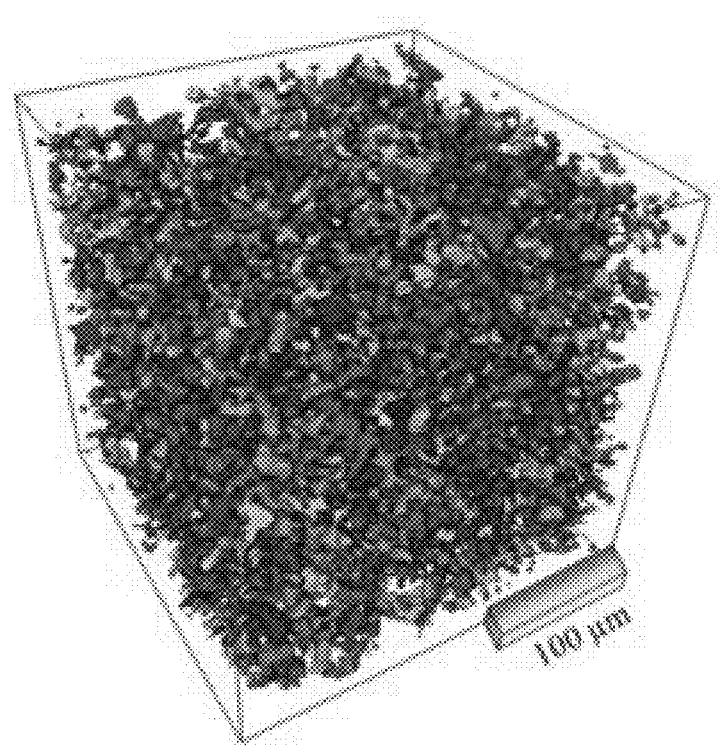
FIG. 2(b) illustrates the isolated pores for digital pore size distribution calculation, color coded by size.
Figure 3:
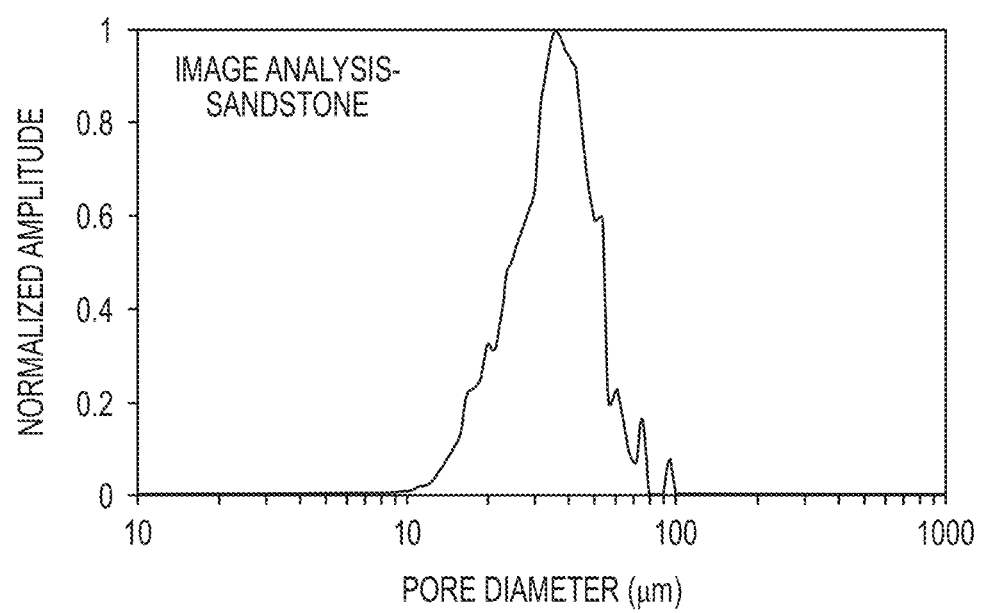
FIG. 3 illustrates a digitally calculated pore size distribution of the constructed Sandstone rock model by image analysis.

The NMR $T_2$ response in two 3D rock models of Brea sandstone and mudrock has been simulated using the random walk simulation. The constructed rock model with about 300×300×300 voxel (about 1 µm resolution) and about 16.86 p.u. porosity is illustrated in FIG. 2(a). However any range at which the image can be made can be used with embodiments of the present invention. The isolated pores for digital pore size distribution calculation are color coded by size and are illustrated in FIG. 2(b). FIG. 3 illustrates a uni-modal pore size distribution. The distribution was digitally calculated by image analysis illustrates a uni-modal pore size distribution of between about 10 µm and about 100 µm with a mode of about 35 µm.

Simulation Results

Figure 4:
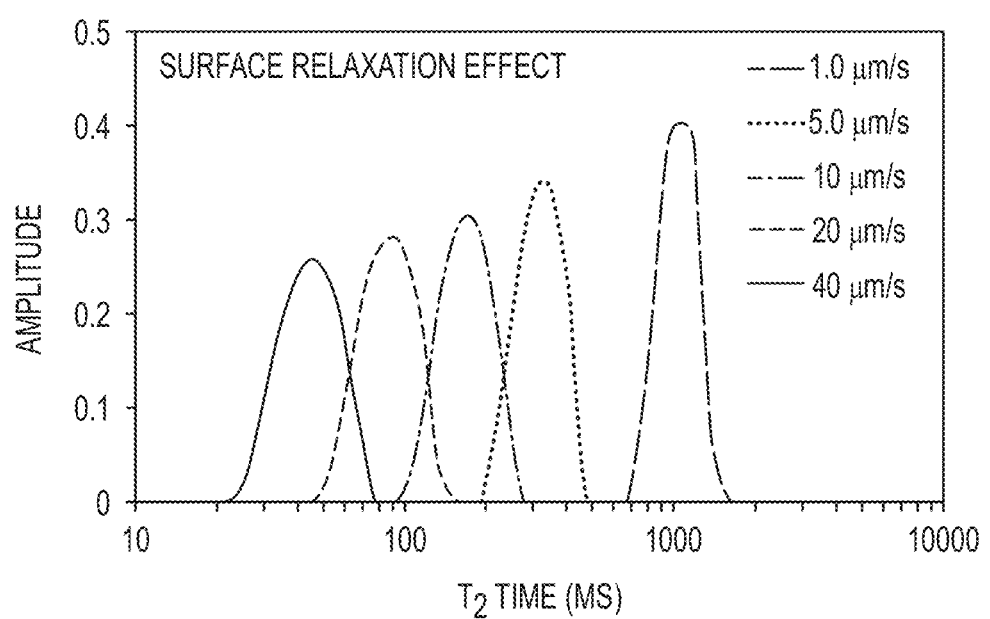
FIG. 4 illustrates the effect of surface relaxivity on NMR response in sandstone model.

Since saturating bulk fluid and image resolution size are both known values in laboratory NMR experiments, surface relaxation is the main variable factor to match the simulation with measurements in these practices. FIG. 4 illustrates the effect of surface relaxivity on NMR response in a sandstone model. In this simulation, de-ionized water bulk relaxation (about 2500 msec) and diffusion coefficients (about 2.5× 10-9 m2/s) have been used as the saturating fluid and the image resolution is chosen as about 1 µm. As expected by increasing the surface relaxivity, the NMR response shifts towards faster times.

FIG. 4 illustrates an increase in the surface relaxivity the NMR response for faster rates. In the simulation illustrated in FIG. 4, de-ionized water bulk relaxation (about 2500 ms) and diffusion coefficient (about $2.5 \times 10^{-9}$ m$^2$/s) have been used as the saturating fluid and the image resolution is chosen as about 1 µm.

Figure 5:
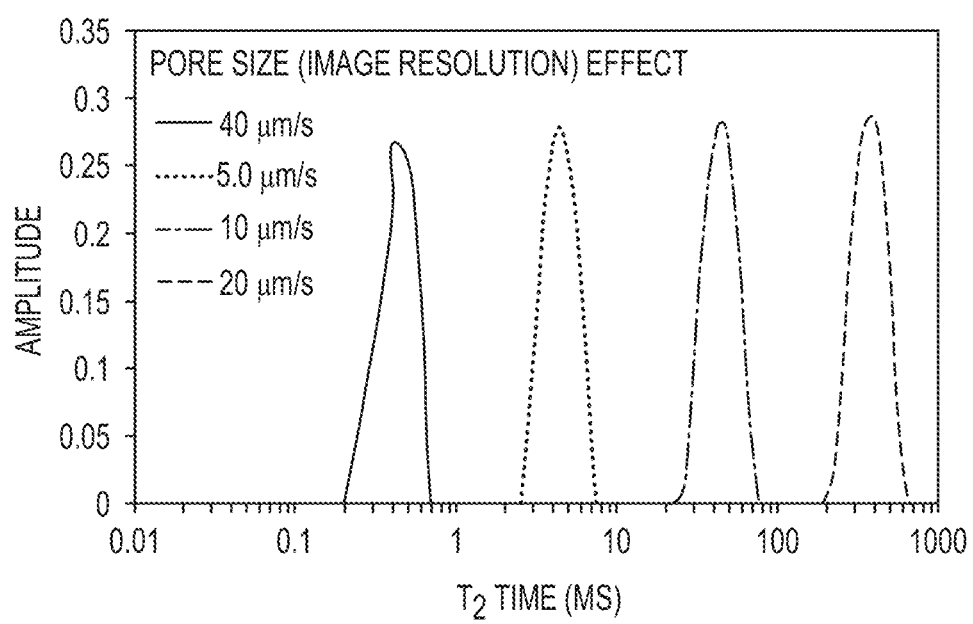
FIG. 5 illustrates the effect of pore size on the NMR response.

FIG. 5 illustrates the effect of pore size (or in this case image resolution) on the NMR response. The simulation is performed assuming deionized water as the saturation fluid and the surface relaxivity of about 20 µm/s. The resolution of the voxels has changed from about 5 nm to 5000 nm. As expected, decreasing the resolution increases the surface relaxivity and consequently the relaxation rate in the sample. Since surface relaxivity is the dominant relaxation mechanism in water saturated samples, the NMR spectra shifts towards the faster relaxation times as a result of decreasing the resolution.

The foregoing description of the present invention has been presented for purposes of illustration and description. Furthermore, the description is not intended to limit the invention to the form disclosed herein. Consequently, variations and modifications commensurate with the above teachings, and the skill or knowledge of the relevant art, are within the scope of the present invention. The embodiment described hereinabove is further intended to explain the best mode known for practicing the invention and to enable others skilled in the art to utilize the invention in such, or other, embodiments and with various modifications required by the particular applications or uses of the present invention. It is intended that the appended claims be construed to include alternative embodiments to the extent permitted by the prior art.

What is claimed is:

1. A method to directly calculate a pore size distribution in a hydrocarbon reservoir using a nuclear magnetic resonance (NMR) system, comprising:
  providing a sample of the hydrocarbon reservoir to the NMR system to produce an image;
  determining a simulated $T_2$ distribution from the image by varying a number of $T_2$ peaks and a relaxation rate;
  determining an experimental $T_2$ distribution by placing at least one rock sample from the hydrogen reservoir in a magnetic field to produce an oriented state of a hydrogen nuclei, subjecting the at least one sample to a sequence of pulses, and determining the relaxation time of the hydrogen nuclei from the oriented state to a normal state of the hydrogen nuclei;

determining a surface relaxivity with the simulated $T_2$ distribution and the experimental $T_2$ distribution;

determining the pore size distribution with the surface relaxivity; and comparing the surface relaxivity with an experimental pore size distribution to determine the pore size distribution in the hydrocarbon reservoir.

2. The method of claim 1, further comprising comparing the surface relaxivity with a laboratory NMR response to determine an adjusted surface relaxivity.

3. The method of claim 2, further comprising converting a NMR size distribution to the pore size distribution with the adjusted surface relaxivity.

4. The method of claim 2, wherein the laboratory NMR response is a NMR surface relaxivity.

5. The method of claim 1, further comprising comparing an independent pore size distribution measurement with the pore size distribution.

6. The method of claim 5, wherein the independent pore size distribution measurement is obtained by at least one of mercury intrusion or nitrogen adsorption.

7. The method of claim 1, further comprising determining the experimental pore distribution size distribution with a gas adsorption.

8. The method of claim 1, further comprising determining the experimental pore distribution with a mercury intrusion porosimetry.

9. The method of claim 1, wherein the hydrocarbon reservoir comprises shale.

10. The method of claim 9, wherein the shale is a siliciclastic mudrock.

11. The method of claim 9, wherein the shale is carbonate mudrock.

12. The method of claim 1, wherein in the hydrocarbon reservoir comprises sandstone.

13. The method of claim 1, further comprising determining an adjusted surface relaxivity from the surface relaxivity and a NMR surface relaxivity.

14. The method of claim 13, wherein the pore size distribution is determined with the adjusted surface relaxivity.

15. The method of claim 1, wherein the simulated $T_2$ distribution is uni-modal.

16. The method of claim 1, wherein the simulated $T_2$ distribution is bi-modal.

17. The method of claim 1, wherein the sequence of pulses comprise short gradient pulses.

18. The method of claim 1, wherein the sequence of pulses comprise radio frequency pulses and delay times.

19. The method of claim 1, wherein the sequence of pulses comprises Carr-Purcell-Meiboom-Gill pulse sequences.

* * * * *